US005843758A

United States Patent [19]
Russell et al.

[11] Patent Number: 5,843,758
[45] Date of Patent: Dec. 1, 1998

[54] ENZYME BASED BIOREMEDIATION

[75] Inventors: Robyn Joyce Russell, Wanniassa; Richard David Newcomb, Sutton; Geoffrey Charles de Quetteville Robin, Aranda; Thomas Mark Boyce; Peter Malcolm Campbell, both of Cook, all of Australia; Anthony Gerard Parker, Davis, Calif.; John Graham Oakeshott, Wanniassa; Kerrie-Ann Smyth, Cook, both of Australia

[73] Assignee: The Commonwealth of Australia Commonwealth Scientific and Industrial Research Organization, Campbell, Australia

[21] Appl. No.: 669,524

[22] PCT Filed: Jan. 13, 1995

[86] PCT No.: PCT/AU95/00016

§ 371 Date: Oct. 7, 1996

§ 102(e) Date: Oct. 7, 1996

[87] PCT Pub. No.: WO95/19440

PCT Pub. Date: Jul. 20, 1995

[30] Foreign Application Priority Data

Jan. 13, 1994 [AU] Australia ................ PM 3347

[51] Int. Cl.$^6$ ............... C12N 1/20; C12N 9/16; C12N 12/00; B09B 3/00
[52] U.S. Cl. ........... 435/252.3; 435/196; 435/320.1; 435/71.1; 435/262; 435/262.5; 536/23.2; 530/350
[58] Field of Search .................. 435/196, 6, 69.1, 435/252.3, 320.1, 71.1, 91.1, 262, 262.5; 536/23.2; 530/350

[56] References Cited

FOREIGN PATENT DOCUMENTS

89/02920  4/1989  WIPO.
90/02177  3/1990  WIPO.

OTHER PUBLICATIONS

Merrin E. Spackman et al., "A Cluster of Esterase Genes on Chromosome 3R of Drosophila Melanogaster Includes Homologues of Esterase Genes Conferring Insecticide Resistance in Lucilia Cuprina"., Dec. 1993., pp. 39–62.
Steven Whyard et al., "Insecticide Resistance and malathion Carboxylesterase in the Sheep Blowfly, Lucilia Cuprina"., Oct. 1993., pp. 9–24.
Kerrie–Ann Smyth et al., "Genetics of Insecticide Resistance"., pp. 1–18.
Joel L. Sussman et al., "Atomic Structure of Acetylcholinesterase From Torpedo California: A Prototypic Acetylcholine–Binding Protein"., pp. 872–878.
Anthony G. Parker. et al., "Biochemistry and Physiology of Esterases in Organoposphate–Susceptible and Resistant Strains of the Australian Sheep Blowfly, Lucilia Cuprina."., 1991 pp. 305–318.
Y.C. Crozier et al., "An Improved Test for Africanized Honybee Mitochondrial DNA."., Mar. 4, 1991., pp. 968–969.
David F. Westneat et al., "Improved Hybridization Conditions for DNA Fingerprints Probed With M13.", Mar. 23, 1988. p. 4161.
James W. Ajioka et al., "Drosophila Genoma Project: One–Hit Coverage in Yeast Artificial Chromosomes." Mar. 14, 1991., pp. 495–509.
U.K. Laemmli. "Cleavage of Structural Proteins During the Assembly of the Head of Bacteriophage T4." Aug. 15, 1970., pp. 680–685.
P.B. Hughes et al., Genetics of an Esterase Associated with Resistance to Oranoposphorus Insecticides in the Sheep Blowfly, Lucilia Cuprina(Wiedemann) (Diptera: Calliphoridae.) 1985 pp. 535–544.
R. Ziegler et al., "General Esterase, Malathion Carboxylesterase, and malathion Resistance in Culex Tarsalis.", 1987 279–285.
D. A. Raftos "The Biochemical Basis of Malathion Resistance in the Sheep Blowfly, Lucilia Cuprina." Feb. 7, 1986.pp.303–309.
Marion M. Bradford., "A Rapid and Sensitive Method for the Quantitation of Microgram Quantities of Protein Utilizing the Principle of Protein–Dye Binding." Jan. 29, 1976., pp. 248–254.
Andrew P. Feinberg et al., "A Technique for Radiolabeling DNA Restriction Endonuclease Fragments to High Specific Activity." Sep. 7, 1982.pp. 6–6–13.
J. Sambrook et al., "A Laboratory Manual 2nd Edition, Cold Spring Harbor Laboratory Press USA." 1989 pp. 7.26–7.29.
John M. Chirgwin et al., "Isolation of Biologically Active Ribonucleic Acid From Sources Enriched in Ribonuclease." pp. 5294–5299.
Parker et al. (1991) Pesticide Biochemistry and Physiology 41, 305–318.

Primary Examiner—Robert A. Wax
Assistant Examiner—Tekchand Saidha
Attorney, Agent, or Firm—McDermott, Will & Emery

[57] ABSTRACT

The present invention provides an E3 esterase from an organophosphate resistant strain of L. cuprina. The invention further provides DNA sequences encoding such E3 esterases and cells transformed with the DNA sequences. In addition, the invention relates to the use of the enzyme and transformed cells as bioremediation agents.

17 Claims, No Drawings

ENZYME BASED BIOREMEDIATION

This application is a 371 of PCT/AU94/00016 filed Jan. 1, 1995.

This invention relates to enzymes capable of hydrolysing organophosphate and/or carbamate pesticide residues. In particular, it relates to esterase enzymes purified from organophosphate resistant strains of *Lucilia cuprina,* and isolated DNA molecules encoding such enzymes.

Residues of organophosphates and carbamate pesticides are undesirable contaminants of the environment and a range of commodities. Areas of particular sensitivity include contamination of domestic water supplies, residues above permissible levels in meat and horticultural exports and contamination of health products like lanolin. Bioremediation strategies are therefore required for eliminating or reducing these pesticide residues. One proposed strategy involves the use of enzymes capable of immobilising or degrading the pesticide residues. Such enzymes may be employed, for example, in bioreactors through which contaminated water could be passed; in sheep or cattle dips to reduce problems with contaminated pasture and run off into water supplies; in the wool scour process to reduce contamination of liquid effluent, wool grease and lanolin; or in washing solutions after post harvest disinfestation of fruit and vegetables to reduce residue levels and withholding times. Suitable enzymes for degrading pesticide residues include esterases. It is desirable that the esterases be relatively specific and hydrolyse the pesticide residues at a rapid rate.

Esterases in insects have been implicated in reproductive behaviour, pheromone and hormone metabolism, digestion, neurotransmission, and in the action of, and resistance to, insecticides, particularly organophosphates (OPs). Three different mechanisms of OP resistance in insects involving esterases have been proposed. One such mechanism involves possible alterations to the structure of an esterase to increase its ability to degrade OPs. This mechanism has been proposed for the house fly, *Musca domestica* and *Lucilia cuprina*. The proposed structural changes are thought to have resulted in the loss of activity for synthetic substrates, such as α-naphthyl acetate and its related esters. For example, esterase E3 in *L. cuprina* has lost the ability to utilize α- and β-naphthyl acetate as substrates in all the OP-resistant strains examined to date. However, concomitantly with this loss in ability to utilise α- and β-naphthyl acetate substrates, it would appear that the OP-resistant E3 esterase becomes capable of hydrolysing OPs into non-toxic products whereas the susceptible E3 esterase cannot. Thus, the E3 esterase from OP-resistant strains of *L. cuprina* may be a suitable enzyme for development as a catalytic bioremediant for organophosphates and/or carbamates.

The present inventors have now developed a method for purifying the E3 esterase from *L. cuprina*. Kinetic data obtained from assays using homogenates suggests that the E3 esterase from OP-resistant strains of *L. cuprina,* hydrolyses OPs quickly even under suboptimal conditions (prevalent in most bioremediation applications). Further, the inventors have isolated the gene encoding the E3 esterase from an OP-susceptible and resistant strains of *L. cuprina,* and identified a homologue of this gene in *Drosophila melanogaster*.

Accordingly, in a first aspect the present invention consists in an E3 esterase from an organophosphate-resistant strain of *Lucilia cuprina,* in substantially pure form.

Preferably, the E3 esterase is from one of the isochromosomal OP-resistant *L. cuprina* strains selected from the group consisting of der-S, Inverell 22, Landillo 103 and Sunbury 5.2.

In a second aspect, the invention provides an isolated DNA molecule comprising a nucleotide sequence encoding a *Lucilia cuprina* E3 esterase or portion thereof capable of hydrolysing organophosphates and/or carbamate pesticide residues.

Preferably, the isolated DNA molecule comprises a nucleotide sequence encoding an E3 esterase or portion thereof, from an OP-resistant strain of *L. cuprina* (such as those strains listed above). More preferably, the isolated DNA molecule includes a nucleotide sequence substantially as shown in Table 1 from an OP-resistant strain of *L. cuprina* (SEQ ID NO:1).

The inventors have also identified a homologue of this gene in *D. melanogaster*. This homologue encodes esterase EST23 which shares biochemical, physiological and genetic properties with E3 esterase from *L. cuprina*. Like E3, the *D. melanogaster* EST23 is a membrane-bound α-esterase which migrates slowly towards the anode at pH 6.8. Both enzymes have similar in vitro preferences for substrates with shorter acid side chain length. Furthermore, they both show high sensitivity to inhibition by paraoxon and insensitivity to inhibition by eserine sulphate. The activity of each enzyme peaks early in development and again, in the adult stage. Both enzymes are found in the male reproductive system and larval and adult digestive tissues, the latter being consistent with a role for these enzymes in organophosphate resistance. Fine structure deficiency mapping localised EST23 to cytological region 84D3 to E1-2 on the right arm of chromosome 3 (Spackman, M. E., Oakeshott, J. G., Smyth, K-A, Medveczky, K. M. and Russell, R. J. (1994) Biochemical Genetics 32: 39–62).

Orthologs of the E3 encoding sequence may also be present in the genome of other insects, and particularly other species of Diptera. Thus, it is to be understood that the invention also extends to these orthologs.

The isolated DNA molecules according to the second aspect of the present invention may be cloned into a suitable expression vector and subsequently transfected into a prokaryotic or eukaryotic host cell for expression of the esterase. A particularly suitable system involves baculovirus vectors and an insect cell line.

The invention further relates to methods for eliminating or reducing the concentration of organophosphate and/or carbamate pesticide residues in a contaminated sample or substance, involving the use of an esterase according to the first aspect or an esterase encoded by an isolated DNA molecule according to the second aspect.

It is also envisaged that as an alternative to using the esterase per se as a bioremediation agent the bioremediation agent may be an organism transformed with the DNA encoding the esterase. In such an arrangement the organism transformed such that it expresses the esterase would be used as the bioremediation agent.

In addition, the enzyme of the present invention may be used in in vitro assays for identifying resistance breakers amongst an array of alternative organophosphates and esterase inhibitors. By using the enzyme of the present invention, organophosphates can be screened for resistance to the enzyme activity. Such organophosphates could then be used in situations where resistance is of concern.

In order that the nature of the present invention may be more clearly understood preferred forms thereof will now be described with reference to the following non-limiting examples.

EXAMPLE 1

Determination in *Lucilia cuprina* of Diethyl Phosphate from Esterase Hydrolysis of Paraoxon Diethyl phosphate from esterase hydrolysis of paraoxon was determined accurately by capillary gas chromatography/chemical ionisation mass spectrometry, using specially synthesised diethyl-$^2$H$_{10}$ phosphate as internal standard.

Samples of resistant and susceptible *L. cuprina* homogenates were incubated with paraoxon for defined periods (q.v.), then snap-frozen to quench further metabolism. A known quantity of internal standard was added to each sample, which was then extracted twice by vortex-mixing with dichloromethane (100 μl) to denature the proteins and to remove lipophiles, including any remaining paraoxon. The aqueous layer was separated and evaporated to dryness under a nitrogen stream. The residue was vortex-mixed with 75 μl acetonitrile for 15 min, transferred to a 100 μl glass conical vial and again evaporated to dryness under nitrogen. The residue was taken up in 30 μl acetonitrile and 5 μl N-methyl-N-tert-butyldimethylsilyl trifluoroacetamide added. The capped vial was vortex-mixed for 30 min at room temperature (25° C.) and the solution was then extracted with pentane (20 μl). The separated pentane layer was washed once with acetonitrile (10 μl) and stored at −20° C. prior to mass spectrometry. Samples were introduced to the mass spectrometer (VG 70-70) by way of a directly coupled Hewlett Packard 5790 gas chromatograph, using cool on-column injection at 30° C. to a 5% phenyl methylsilicone column (DB5, 30 m by 0.32 mm ID, 1.0 μm phase thickness) preceded by a 4 m retention gap. Silylated diethyl phosphate and its internal standard were eluted during temperature programming and detected for quantitative analysis in the mass spectrometer by selected ion monitoring of their respective $(M+H)^+$ ions generated by positive-ion chemical ionisation using ammonia as reagent plasma.

The results of the GC/MS assay for degradation of paraoxon by crude homogenates of Lucilia strains indicate two significant processes. First, hydrolysis of paraoxon into the diethyl phosphate (DEP) and para-nitrophenol moieties occurs at a rapid rate. Within the first minute of the assay significantly more DEP was produced by the homogenate of the resistant strain (ca. 1.3 nmol by Inverell 22) than the susceptible strain (ca. 0.95 nmol LBB101). Each of these strains are iso-chromosomal for the fourth chromosome, and thus are homozygous for the alternate alleles of the resistance-conferring enzyme, E3. Thus, the difference in hydrolysis is indicative of differences at that locus.

The second, and surprising, result is that free DEP, which is what the assay measures, is rapidly sequestered or enzymatically altered after its release from paraoxon by E3. This activity is indicated by the steadily decreasing amount of free DEP over the course of the experiment. This activity is apparently not as rapid as the hydrolysis by E3, but is more stable in that it continues to remove DEP from solution in the face of hydrolysis of paraoxon. That this activity is actually non-specific binding of DEP to heterogeneous protein in the homogenate is suggested by the loss of DEP from the boiled control, where no enzymatic activity is expected. To the extent that our ability to monitor hydrolysis is compromised by the binding of DEP to heterogeneous protein, it may be the case that the hydrolysis is significantly more rapid than estimated.

EXAMPLE 2

Purification of Esterase 3 (E3) from OP-Sensitive
Lucilia cuprina

Homogenisation, Differential Centrifugation and Solubilisation of E3

The starting material was 200 g of previously frozen, adult L. cuprina. Heads were removed by sieving and the thorax and abdomen retained. The latter were homogenised in fractionation butter (50 mM Tris/HCl buffer, pH 7.5, 25 mM KCl, 5 mM Mg.acetate, 350 mM sucrose, 0.5 mM phenylthiourea) on ice in a Sorvall blender. The homogenate was clarified by filtration through gauze then centrifugation (15000 g, 30 minutes). The homogenate was recentrifuged (120000 g, 70 minutes) and the pellet was resuspended in 100 mM imidazole/HCl (pH 7.0) containing 1 mM EDTA and 0.05% (v/v) Triton X-100. This suspension was frozen (−20° C., overnight) and thawed to solubilise E3. Insoluble material was removed by centrifugation (15000 g, 30 minutes) and filtration (0.45 μm).

Chromatographic Steps

Three chromatographic purification steps were performed using the Pharmacia FPLC system to control buffer flow rates and gradients. Firstly, anion exchange was performed using DEAE-sepharose equilibrated with 20 mM imidazole/HCl (pH 7.0) containing 0.1% v/v Triton X-100, 10% v/v glycerol and E3 was eluted using a gradient of this solution containing 0–1M NaCl. E3 containing fractions were pooled and subjected to gel filtration using a Superdex 200 (Pharmacia) column equilibrated and eluted with 50 mM imidazole/HCl (pH 7.0) containing 0.1% v/v Triton X-100 and 10% v/v glycerol. E3 containing fractions were pooled and a second anion exchange separation was performed using a Mono Q column (strong anion exchanger, Pharmacia) with the same buffers as the first anion exchange separation.

Electrophoretic Steps

An E3 containing fraction from the final chromatographic separation was concentrated and subjected to non-denaturing polyacrylamide gel electrophoresis (PAGE) (Hughes and Raftos, 1985). The region of the gel containing E3 activity was excised. Separation by denaturing PAGE (Laemmli, 1970) and silver staining for total protein (Biorad Silver Stain kit) revealed that a single polypeptide of 70 kDa was present in the region of the non-denaturing gel containing E3.

In a modification of the above protocol, a selective precipitation step is added after solubilisation of E3. Insoluble material is removed by centrifugation as above then an equal volume of 16% polyethylene glycol (PEG, average MW=2000) is added in 10 mM imidazole/HCl (pH 7.0) containing 10% glycerol. The solution is incubated on ice for 1 hour then centrifuged (10000 g, 15 minutes).

The 8% PEG precipitate is resuspended in about 20 ml of 10 mM imidazole/HCl (pH 7.0) containing 10% glycerol and subjected to isoelectric focussing (IEF). IEF is performed using a Biorad "Rotofor" apparatus. Three ml of ampholytes (Pharmalyte pH 4–6.5, Pharmacia) and 10% glycerol were added to partially purified E3, bringing the total volume to 50ml, the volume of the Rotofor focussing chamber. An antifreeze solution at −8° C. is circulated through the apparatus to achieve a temperature in the focussing chamber of around 2° C. The sample is focussed for 4 hours at 12 watts, during which time the voltage rises from around 300 to 900 volts. Twenty 2.5 ml fractions are harvested and E3 is found to focus and precipitate at around pH 4.9. The E3 containing fractions are pooled and centrifuged (1000 g, 15 minutes). The pellet is first resuspended and centrifuged in buffer lacking Triton X-100 (10000 g, 15 minutes), then in the same buffer containing 1% Triton X-100. The supernatant from the last centrifugation is retained for anion exchange chromatography.

Anion exchange chromatography is performed as described above using the Mono Q column and the DEAE column is omitted. A further gel filtration step (e.g. using a Pharmacia Superose 6 column) and electrophoresis as described above, may be required at this stage.

EXAMPLE 3

Isolation and Cloning of the Gene Encoding OP-Sensitive L. cuprina* E3

The E3 gene of *L. cuprina* has been mapped using classical genetic techniques to chromosome 4 (Raftos D. A., Pesticide Biochemistry and Physiology Vol. 26:302, 1986), and the likely homologue of E3 in *D. melanogaster*, EST23, has been mapped to the right arm of chromosome 3 in the vicinity of the gene encoding the major α-carboxylesterase, EST9. Chromosome 3R in *D. melanogaster* is homologous to chromosome 4 in *L. cuprina*. The EST9 gene had been mapped previously to cytological location 84D3-5. Fine structure deficiency mapping experiments were used to localise EST23 to cytological region 84D3 to E1-2, the region encompassing EST9 (Spackman et al, 1994).

In order to clone the E3 gene from *L. cuprina,* it was decided to use the molecular genetic techniques available for *D. melanogaster* to clone the E3 homologue and use these clones as probes to isolate the *L. cuprina* genes themselves.

The route which proved productive used a yeast artificial chromosome (YAC) clone (termed DY219) containing 300 kb of DNA from the 84D3-10 region of chromosome 3R (Ajioka, J. W., Smoller, D. A., Jones, R. W., Carulli, J. P., Vallek, A. E. C., Garza, D., Link, A. J., Duncan, I. W. and Hartl, D. L., Chromosoma 100:495, 1991).

This resulted in the isolation of a 90 kb stretch of DNA containing 11 regions of homology to consensus esterase oligonucleotide probes, defining 10 esterase genes.

In order to clone the homologous *L. cuprina* esterase genes, cluster-specific esterase primers were synthesised and used in PCR reactions to amplify the relevant genes from both *L. cuprina* genomic DNA and cDNA. Reactions were carried out under standard conditions:

|  | Final concentration/amount |
| --- | --- |
| Template DNA | 100–1000 ng |
| primer A* | 1 n mole |
| primer B* | 1 n mole |
| Buffer | 10 mM Tris-HCl (pH 8.3), 1.5 mM MgCl$_2$, 50 mM KCl |
| dNTP's | 0.2 mM each |
| Taq polymerase | 2 units |
| Total Volume | 50 µl |

*Primer pairs for experiments involving genomic DNA were:
Primer A: 5' GGIWSIGARGAYTGYYTITAYYTNAAYGTNTA 3' (SEQ ID NO: 5)
Primer B: 5' YTGRTCYTTIARICCIGCRTTNCCNGGNAC 3' (SEQ ID NO: 6)
Primer pairs for experiments involving cDNA were:
Primer A: 5' ATHCCITWTGCIVMICCICCIBTNGG 3' (SEQ ID NO: 7)
Primer B: as for genomic DNA experiment.
Note:
IUB codes for mixed positions are used.
I = inosine, which was used in positions of 4-fold redundancy
PCR conditions:
97° C. 35" 45° C. 2' 60° C. 2' 3 cycles
97° C. 35" 50° C. 2' 72° C. 1' 27–37 cycles Reaction products were visualised by agarose gel electrophoresis.

Bands unique to 2 primer reactions from genomic DNA were gel-purified and subjected to a further 30 rounds of amplification. Resultant bands were then gel purified, cloned and sequenced. Bands derived from genomic DNA varied in size, the differences presumably resulting from the presence of introns at two potential sites between all four possible combinations of primers. The four major bands obtained were cloned and sequenced and all were shown to contain esterase encoding sequences.

CDNA derived from late larval fat bodies (known to be enriched for the E3 protein) were chosen as templates in PCR reactions. Bulk DNA was prepared from a cDNA library of the tissue and PCR reactions were carried out as for genomic DNA, except that the candidate esterase fragments could be identified directly by their characteristic size as predicted from *D. melanogaster* sequence data.

In summary, five esterase amplicons were isolated from *L. cuprina* genomic DNA. One of these (LcαE7) was also isolated from larval fat body cDNA and showed direct homology with gene DmaE7 of the *D. melanogaster* cluster. This *L. cuprina* cluster member (LcαE7) was chosen as a candidate for the gene E3 as Northern blot analysis showed that it is expressed in the same life stages as those exhibiting E3 enzyme activity.

One cDNA has been cloned from a larval fat body CDNA library and six more have been cloned from a pupal cDNA library. One of the pupal cDNAs was probably full-length and therefore sequenced completely. Table 1 shows the DNA and inferred amino acid sequence of the OP-sensitive E3 (clone Lc743) and Table 2 shows the level of inferred amino acid similarity between *D. melanogaster* DmaE7 (SEQ ID NO:8) and LcαE7 (clone Lc743) (SEQ ID NO:3).

The pupal LcαE7 cDNA has now been expressed using a baculovirus vector transfected into an insect cell line (see below for details of method). The expression product was run on a PAGE and stained strongly with α- and β-naphthyl acetate. This result confirmed that LcαE7 encodes a susceptible E3 esterase.

Table 1. Multiple nucleotide alignment of the four diazinon-resistant clones (L103A-D) (SEQ ID NO:2) and consensus (L103con) with the reference susceptible clone (Lc743) of LcαE7 (E3). Dots indicate identity with the Lc743 susceptible clone and a dash in the sequence represents a missing nucleotide. Below the ruler is the aligned nucleotide sequence and above is the inferred amino acid sequence of Lc743 with the five replacements found in Lc7L103con indicated in bold text immediately below. Nucleotides are numbered from the translation start site.

TABLE 1

Multiple nucleotide alignment of the four diazinon-resistant clones (L103A–D) and consensus (L103con) with the reference susceptible clone (Lc743) of LcαE7 (E3). Dots indicate identity with the Lc743 susceptible clone and a dash in the sequence represents a missing nucleotide. Below the ruler is the aligned nucleotide sequence and above is the inferred amino acid sequence of Lc743 with the five replacements found in Lc7L103con indicated in bold text immediately below. Nucleotides are numbered from the translation start site.

| Lc743 | M | N | F | N | V | S | L | M | E | K | L | K | W | K | I | K | C | I | E | N |
| --- | --- | --- | --- | --- | --- | --- | --- | --- | --- | --- | --- | --- | --- | --- | --- | --- | --- | --- | --- | --- |
| L103con | . | . | . | . | . | . | . | . | . | . | . | . | . | . | . | . | . | . | . | . |
| 1 | ----------+---------+---------+---------+---------+---------+ 60 |

TABLE 1-continued

| | |
|---|---|
| Lc743 | ATGAATTTCAACGTTAGTTTGATGGAGAAATTAAAATGGAAGATTAAATGCATTGAAAAT |
| L103A | .............................................................. |
| L103B | .............................................................. |
| L103C | .............................................................. |
| L103D | .............................................................. |
| L103con | .............................................................. |

| | | | | | | | | | | | | | | | | | | | | |
|---|---|---|---|---|---|---|---|---|---|---|---|---|---|---|---|---|---|---|---|---|
| Lc743 | K | F | L | N | Y | R | L | T | T | N | E | T | V | V | A | E | T | E | Y | G |
| L103con | . | . | . | . | . | . | . | . | . | . | . | . | . | . | . | . | . | . | . | . |

61 ----------+---------+---------+---------+---------+---------+ 120

| | |
|---|---|
| Lc743 | AAGTTTTTAAACTATCGTTTAACTACCAATGAAACGGTGGTAGCTGAAACTGAATATGGC |
| L103A | .............................................................. |
| L103B | .............................................................. |
| L103C | .............................................................. |
| L103D | ....................C......................................... |
| L103con | .............................................................. |

| | | | | | | | | | | | | | | | | | | | | |
|---|---|---|---|---|---|---|---|---|---|---|---|---|---|---|---|---|---|---|---|---|
| Lc743 | K | V | K | G | V | K | R | L | T | V | Y | D | D | S | Y | Y | S | F | E | G |
| L103con | . | . | . | . | . | . | . | . | . | . | . | . | . | . | . | . | . | . | . | . |

121 ----------+---------+---------+---------+---------+---------+ 180

| | |
|---|---|
| Lc743 | AAAGTGAAAGGCGTTAAACGTTTAACTGTGTACGATGATTCCTACTACAGTTTTGAGGGT |
| L103A | .............................................................. |
| L103B | .............................................................. |
| L103C | .............................................................. |
| L103D | .............................................................. |
| L103con | .............................................................. |

| | | | | | | | | | | | | | | | | | | |
|---|---|---|---|---|---|---|---|---|---|---|---|---|---|---|---|---|---|---|
| Lc743 | I | P | Y | A | Q | P | P | V | G | E | L | R | F | K | A | P | Q | R | P | T |
| L103con | . | . | . | . | . | . | . | . | . | . | . | . | . | . | . | . | . | . | . | . |

181 ----------+---------+---------+---------+---------+---------+ 240

| | |
|---|---|
| Lc743 | ATACCGTACGCCCAACCGCCAGTGGGTGAGCTGAGATTTAAAGCACCCCAGCGACCAACA |
| L103A | .............................................................. |
| L103B | .............................................................. |
| L103C | .............................................................. |
| L103D | ........................................................A.... |
| L103con | .............................................................. |

| | | | | | | | | | | | | | | | | |
|---|---|---|---|---|---|---|---|---|---|---|---|---|---|---|---|---|---|
| Lc743 | P | W | D | G | V | R | D | C | C | N | H | K | D | K | S | V | Q | V | D | F |
| L103con | . | . | . | . | . | . | . | . | . | . | . | . | . | . | . | . | . | . | . | . |

241 ----------+---------+---------+---------+---------+---------+ 300

| | |
|---|---|
| Lc743 | CCCTGGGATGGTGTGCGTGATTGTTGCAATCATAAAGATAAGTCAGTGCAAGTTGATTTT |
| L103A | .............................................................. |
| L103B | .............................................................. |
| L103C | .............................................................. |
| L103D | .............................................................. |

TABLE 1-continued

| | | | | | | | | | | | | | | | | |
|---|---|---|---|---|---|---|---|---|---|---|---|---|---|---|---|---|
| L103con | . | . | . | . | . | . | . | . | . | . | . | . | . | . | . | |
| Lc743 | I | T | G | K | V | C | G | S | E | D | C | L | Y | L | S | V | Y | T | N | N |
| L103con | . | . | . | . | . | . | . | . | . | . | . | . | . | . | . | . | . | . | . | . |

```
       301 ----------+----------+----------+----------+----------+----------+ 360
Lc743      ATAACGGGCAAAGTGTGTGGCTCAGAGGATTGTCTATACCTAAGTGTCTATACGAATAAT
L103A      ..T..A......................................C...............
L103B      ..T..A......................................C...............
L103C      ..T..A......................................C...............
L103D      ..T..A......................................C...............
L103con    ..T..A......................................C...............
```

| Lc743 | L | N | P | E | T | K | R | P | V | L | V | Y | I | H | G | G | F | I | I |
|---|---|---|---|---|---|---|---|---|---|---|---|---|---|---|---|---|---|---|---|
| L103con | . | . | . | . | . | . | . | . | . | . | . | . | . | . | . | D | . | . | . |

```
       361 ----------+----------+----------+----------+----------+----------+ 420
Lc743      CTAAATCCCGAAACTAAACGTCCCGTTTTAGTATACATACATGGTGGTGGTTTTATTATC
L103A      ..........................................A................
L103B      ..........................................A................
L103C      ..........................................A................
L103D      ..........................................A................
L103con    ..........................................A................
```

| Lc743 | G | E | N | H | R | D | M | Y | G | P | D | Y | F | I | K | K | D | V | V | L |
|---|---|---|---|---|---|---|---|---|---|---|---|---|---|---|---|---|---|---|---|---|
| L103con | . | . | . | . | . | . | . | . | . | . | . | . | . | . | . | . | . | . | . | . |

```
       421 ----------+----------+----------+----------+----------+----------+ 480
Lc743      GGTGAAAATCATCGTGATATGTATGGTCCTGATTATTTCATTAAAAAGGATGTGGTGTTG
L103A      ............................................................
L103B      ........................C...................................
L103C      ............................................................
L103D      ............................................................
L103con    ............................................................
```

| Lc743 | I | N | I | Q | Y | R | L | G | A | L | G | F | L | S | L | N | S | E | D | L |
|---|---|---|---|---|---|---|---|---|---|---|---|---|---|---|---|---|---|---|---|---|
| L103con | . | . | . | . | . | . | . | . | . | . | . | . | . | . | . | . | . | . | . | . |

```
       481 ----------+----------+----------+----------+----------+----------+ 540
Lc743      ATTAACATACAATATCGTTTGGGAGCTCTAGGTTTTCTAAGTTTAAATTCAGAAGACCTT
L103A      ............................................................
L103B      ............................................................
L103C      ............................................................
L103D      ............................................................
L103con    ............................................................
```

| Lc743 | N | V | P | G | N | A | G | L | K | D | Q | V | M | A | L | R | W | I | K | N |
|---|---|---|---|---|---|---|---|---|---|---|---|---|---|---|---|---|---|---|---|---|
| L103con | . | . | . | . | . | . | . | . | . | . | . | . | . | . | . | . | . | . | . | . |

```
       541 ----------+----------+----------+----------+----------+----------+ 600
```

TABLE 1-continued

| Lc743 | AATGTGCCCGGTAATGCCGGCCTTAAAGATCAAGTCATGGCCTTGCGTTGGATTAAAAAT | |
|---|---|---|
| L103A | . . . . . . . . . . . . . . . . . . . . . . . . . . . . . . . . . . . . . . . . . . . . . . . . . . . . . . . . . . . . . . . | |
| L103B | . . . . . . . . A . . . . . . . . . . . . . . . . . . . . . . . . . . . . . . . . . . . . . . . . . . . . . . . . . . . . . | |
| L103C | . . . . . . . . . . . . . . . . . . . . . . . . . . . . . . . . . . . . . . . . . . . . . . . . . . . . . . . . . . . . . . | |
| L103D | . . . . . . . . . . . . . . . . . . . . . . . . . . . . . . . . . . . . . . . . . . . . . . . . . . . . . . . . . . . . . . | |
| L103con | . . . . . . . . . . . . . . . . . . . . . . . . . . . . . . . . . . . . . . . . . . . . . . . . . . . . . . . . . . . . . . | |
| | | |
| Lc743 | N  C  A  N  F  G  G  N  P  D  N  I  T  V  F  G  E  S  A  G | |
| L103con | .  .  .  .  .  .  .  .  .  .  .  .  .  .  .  .  .  .  .  . | |
| 601 | - - - - - - - - - - + - - - - - - - - - + - - - - - - - - - + - - - - - - - - - + - - - - - - - - - + - - - - - - - - - + | 660 |
| Lc743 | AATTGCGCCAACTTTGGTGGCAATCCCGATAATATTACAGTCTTTGGTGAAAGTGCCGGT | |
| L103A | . . . . . . . . . . . . . . . . . . . . . . . . . . . . . . . . . . . . . . . . . . . . . . . . . . . . . . . . . . . . . . | |
| L103B | . . . . . . . . . . . . . . . . . . . . . . . . . . . . . . . . . . . . . . . . . . . . . . . . . . . . . . . . . . . . . . | |
| L103C | . . . . . . . . . . . . . . . . . . . . . . . . . . . . . . . . . . . . . . . . . . . . . . . . . . . . . . . . . . . . . . | |
| L103D | . . . . . . . . . . . . . . . . . . . . . . . . . . . . . . . . . . . . . . . . . . . . . . . . . . . . . . . . . . . . . . | |
| L103con | . . . . . . . . . . . . . . . . . . . . . . . . . . . . . . . . . . . . . . . . . . . . . . . . . . . . . . . . . . . . . . | |
| | | |
| Lc743 | A  A  S  T  H  Y  M  M  L  T  E  Q  T  R  G  L  F  H  R  G | |
| L103con | .  .  .  .  .  .  .  .  .  .  .  .  .  .  .  .  .  .  .  . | |
| 661 | - - - - - - - - - - + - - - - - - - - - + - - - - - - - - - + - - - - - - - - - + - - - - - - - - - + - - - - - - - - - + | 720 |
| Lc743 | GCTGCCTCTACCCACTACATGATGTTAACCGAACAAACTCGCGGTCTTTTCCATCGTGGT | |
| L103A | . . . . . . . . . . . . . . . . . . . . . . . . . . . . . . . . . . . . . . . . . . . . . . . . . . . . . . . . . . . . . . | |
| L103B | . . . . . . . . . . . . . . . . . . . . . . . . . . . . . . . . . . . . . . . . . . . . . . . . . . . . . . . . . . . . . . | |
| | | |
| Lc743 | I  L  M  S  G  N  A  I  C  P  W  A  N  T  Q  C  Q  H  R  A | |
| L103con | .  .  .  .  .  .  .  .  .  .  .  .  .  .  .  .  .  .  .  . | |
| 721 | - - - - - - - - - - + - - - - - - - - - + - - - - - - - - - + - - - - - - - - - + - - - - - - - - - + - - - - - - - - - + | 780 |
| Lc743 | ATACTAATGTCGGGTAATGCTATTTGTCCATGGGCTAATACCCAATGTCAACATCGTGCC | |
| L103A | . . . . . . . . . . . . . . . . . . . . . . . . . . . . . . . . . . . . . . . . . . . . . . . . . . . . . . . . . . . . . . | |
| L103B | . . . . . . . . . . . . . . . . . . . . . . . . . . . . . . . . . . . . . . . . . . . . . . . . . . . . . . . . . . . . . . | |
| L103C | . . . . . . . . . . . . . . . . . . . . . . . . . . . C . . . . . . . . . . . . . . . . . . . . . . . . . . . . . . . . . . | |
| L103D | . . . . . . . . . . . . . . . . . . . . . . . . . . . . . . . . . . . . . . . . . . . . . . . . . . . . . . . . . . . . . . | |
| L103con | . . . . . . . . . . . . . . . . . . . . . . . . . . . . . . . . . . . . . . . . . . . . . . . . . . . . . . . . . . . . . . | |
| | | |
| Lc743 | F  T  L  A  K  L  A  G  Y  K  G  E  D  N  D  K  D  V  L  E | |
| L103con | .  .  .  .  .  .  V  .  .  .  .  .  .  .  .  .  .  .  .  . | |
| 781 | - - - - - - - - - - + - - - - - - - - - + - - - - - - - - - + - - - - - - - - - + - - - - - - - - - + - - - - - - - - - + | 840 |
| Lc743 | TTCACCTTAGCCAAATTGGCCGGCTATAAGGGTGAGGATAATGATAAGGATGTTTTGGAA | |
| L103A | . . . . . . . . . . . . . . . . . . . . . T . . . . . . . . . . . . . . . . . . . . . . . . . . . . . . . . . . . . . . . G | |
| L103B | . . . . . . . . . . . . . . . . . . . . . T . . . . . . . . . . . . . . . . . . . . . . . . . . . . . . . . . . . . . . . G | |
| L103C | . . . . . . . . . . . . . . . . . . . . . T . . . . . . . . . . . . . . . . . . . . . . . . . . . . . . . . . . . . . . . G | |
| L103D | . . . . . . . . . . . . . . . . . . . . . T . . . . . . . . . . . . . . . . . . . . . . . . . . . . . . . . . . . . . . . G | |
| L103con | . . . . . . . . . . . . . . . . . . . . . T . . . . . . . . . . . . . . . . . . . . . . . . . . . . . . . . . . . . . . . G | |
| | | |
| Lc743 | F  L  M  K  A  K  P  Q  D  L  I  K  L  E  E  K  V  L  T  L | |

TABLE 1-continued

| | | | | | | | | | | | | | | | | | | | | |
|---|---|---|---|---|---|---|---|---|---|---|---|---|---|---|---|---|---|---|---|---|
| L103con | . | . | L | . | . | . | . | . | . | . | . | . | . | . | . | . | . | . | . | . |

841 ----------+----------+----------+----------+----------+----------+ 900

Lc743    T T T C T T A T G A A A G C C A A G C C A C A G G A T T T A A T A A A A C T T G A G G A A A A A G T T T T A A C T C T A
L103A    . . . . . . T . . . . . . . . . . . . . . . . . . . . . . . . . . . . . . . . . . . . . . . . . . . . . . . . . . . . .
L103B    . . . . . . T . . . . . . . . . . . . . . . . . . . . . . . . . . . . . . . . . . . . . . . . . . . . . . . . . . . . .
L103C    . . . . . . T . . . . . . . . . . . . . . . . . . . . . . . . . . . . . . . . . . . . . . . . . . . . . . . . . . . . .
L103D    . . . . . . T . . . . . . . . . . . . . . . . . . . . . . . . . . . . . . . . . . . . . . . . . . . . . . . . . . . . .
L103con  . . . . . . T . . . . . . . . . . . . . . . . . . . . . . . . . . . . . . . . . . . . . . . . . . . . . . . . . . . . .

| Lc743 | E | E | R | T | N | K | V | M | F | P | F | G | P | T | V | E | P | Y | Q | T |
|---|---|---|---|---|---|---|---|---|---|---|---|---|---|---|---|---|---|---|---|---|
| L103con | . | . | . | . | . | . | . | . | . | . | . | . | . | . | . | . | . | . | . | . |

901 ----------+----------+----------+----------+----------+----------+ 960

Lc743    G A A G A G C G T A C A A A T A A G G T C A T G T T T C C T T T T G G T C C C A C T G T T G A G C C A T A T C A G A C C
L103A    . . . . . . . . . . . . . . . . . . . . . . . . . . . . . . . . . . . . . . . . . . . . . . . . . . . . . . . . . . . .
L103B    . . . . . . . . . . . . . . . . . . . . . . . . . . . . . . . . . . . . . . . . . . . . . . . . . . . . . . . . . . . .
L103C    . . . . . . . . . . . . . . . . . . . . . . . . . . . . . . . . . . . . . . . . . . . . . . . . . T . . . . . . . . . .
L103D    . . . . . . . . . . . . . . . . . . . . . . . . . . . . . . . . . . . . . . . . . . . . . . . . . . . . . . . . . . . .
L103con  . . . . . . . . . . . . . . . . . . . . . . . . . . . . . . . . . . . . . . . . . . . . . . . . . . . . . . . . . . . .

| Lc743 | A | D | C | V | L | P | K | H | P | R | E | M | V | K | T | A | W | G | N | S |
|---|---|---|---|---|---|---|---|---|---|---|---|---|---|---|---|---|---|---|---|---|
| L103con | . | . | . | . | . | . | . | . | . | . | . | . | . | H | . | . | . | . | . | . |

961 ----------+----------+----------+----------+----------+----------+ 1020

Lc743    G C T G A T T G T G T C T T A C C C A A A C A T C C T C G G G A A A T G G T T A A A A C T G C T T G G G G T A A T T C G
L103A    . . . . . . . . . . . . . . . . . . . . . . . . . . . . . . . . . . . . . . . . . . C A . . . . . . . . . . . . . . . .
L103B    . . . . . . . . . . . . . . . . . . . . . . . . . . . . . . . . . . . . . . . . . . C A . . . . . . . . . . . . . . . .
L103C    . . . . . . . . . . . . . . . . . . . . . . . . . . . . . . . . . . . . . . . . . . C A . . . . . . . . . . . . . . . .
L103D    . . . . . . . . . . . . . . . . . . . . . . . . . . . . . . . . . . . . . . . . . . C A . . . . . . . . . . . . . . . .
L103con  . . . . . . . . . . . . . . . . . . . . . . . . . . . . . . . . . . . . . . . . . . C A . . . . . . . . . . . . . . . .

| Lc743 | I | P | T | M | M | G | N | T | S | Y | E | G | L | F | F | T | S | I | L | K |
|---|---|---|---|---|---|---|---|---|---|---|---|---|---|---|---|---|---|---|---|---|
| L103con | . | . | . | . | . | . | . | . | . | . | . | . | . | . | . | . | . | . | . | . |

1021 ----------+----------+----------+----------+----------+----------+ 1080

Lc743    A T A C C C A C T A T G A T G G G T A A C A C T T C A T A T G A G G G T C T A T T T T T C A C T T C A A T T C T T A A G
L103A    . . . . . . . . . . . . . . . . . . . . . . . . . . . . . . . . . . . . . . . . . . . G T . . . . . . . . . .
L103B    . . . . . . . . . . . . . . . . . . . . . . . . . . . . . . . . . . . . . . . . . . . G T . . . . . . . . . .
L103C    . . . . . . . . . . . . . . . . . . . . . . . . . . . . . . . . . . . . . . . . . . . G T . . . . . . . . . .
L103D    . . . . . . . . . . . . . . . . . . . . . . . . . . . . . . . . . . . . . . . . . . . G T . . . . . . . . . .
L103con  . . . . . . . . . . . . . . . . . . . . . . . . . . . . . . . . . . . . . . . . . . . G T . . . . . . . . . .

| Lc743 | Q | M | P | M | L | V | K | E | L | E | T | C | V | N | F | V | P | S | E | L |
|---|---|---|---|---|---|---|---|---|---|---|---|---|---|---|---|---|---|---|---|---|
| L103con | . | . | . | . | . | . | . | . | . | . | . | . | . | . | . | . | . | . | . | . |

1081 ----------+----------+----------+----------+----------+----------+ 1140

Lc743    C A A A T G C C T A T G C T T G T T A A G G A A T T G G A A A C T T G T G T C A A T T T T G T G C C A A G T G A A T T G
L103A    . . . . . . . . . . . . . . . . . . . . . . . . . . . . . . . . . . . . . . . . . . . . . . . . . . . . . . . . . . . .

TABLE 1-continued

| | | | | | | | | | | | | | | | | | |
|---|---|---|---|---|---|---|---|---|---|---|---|---|---|---|---|---|---|
| L103B | . | . | . | . | . | . | . | . | . | . | . | . | . | . | . | . | . |
| L103C | . | . | . | . | . | . | . | . | . | . | . | . | . | . | . | . | . |
| L103D | . | . | . | . | . | . | . | . | . | . | . | . | . | . | . | . | . |
| L103con | . | . | . | . | . | . | . | . | . | . | . | . | . | . | . | . | . |
| | | | | | | | | | | | | | | | | | |
| Lc743 | A | D | A | E | R | T | A | P | E | T | L | E | M | G | A | K | I | K | K | A |
| L103con | . | . | . | . | . | . | . | . | . | . | . | . | . | . | . | . | . | . | . | . |

1141 ----------+---------+---------+---------+---------+---------+ 1200

| Lc743 | GCTGATGCTGAACGCACCGCCCCAGAGACCTTGGAAATGGGTGCTAAAATTAAAAAGGCT |
|---|---|
| L103A | .....A...................................................... |
| L103B | ............................................................ |
| L103C | ............................................................ |
| L103D | ............................................................ |
| L103con | ............................................................ |

| | | | | | | | | | | | | | | | |
|---|---|---|---|---|---|---|---|---|---|---|---|---|---|---|---|
| Lc743 | H | V | T | G | E | T | P | T | A | D | N | F | M | D | L | C | S | H | I | Y |
| L103con | . | . | . | . | . | . | . | . | . | . | . | . | . | . | . | . | . | . | . | . |

1201 ----------+---------+---------+---------+---------+---------+ 1260

| Lc743 | CATGTTACAGGAGAAACACCAACAGCTGATAATTTTATGGATCTTTGCTCTCACATCTAT |
|---|---|
| L103A | ................................C..C....................... |
| L103B | ................................C..C....................... |
| L103C | ................................C..C....................... |
| L103D | ................................C..C....................... |
| L103con | ................................C..C....................... |

| Lc743 | F | W | F | P | M | H | R | L | L | Q | L | R | F | N | H | T | S | G | T | P |
|---|---|---|---|---|---|---|---|---|---|---|---|---|---|---|---|---|---|---|---|---|
| L103con | . | . | . | . | . | . | . | . | . | . | . | . | . | . | . | . | . | . | . | . |

1261 ----------+---------+---------+---------+---------+---------+ 1260

| Lc743 | TTCTGGTTCCCCATGCATCGTTTGTTGCAATTACGTTTCAATCACACCTCCGGTACACCC |
|---|---|
| L103A | ........................A.........................G........ |
| L103B | ........................A................................... |
| L103C | ........................A................................... |
| L103C | ........................A................................... |
| L103D | ........................A................................... |
| L103con | ........................A................................... |

| Lc743 | V | Y | L | Y | R | F | D | F | D | S | E | D | L | I | N | P | Y | R | I | M |
|---|---|---|---|---|---|---|---|---|---|---|---|---|---|---|---|---|---|---|---|---|
| L103con | . | . | . | . | . | . | . | . | . | . | . | . | . | . | . | . | . | . | . | . |

1321 ----------+---------+---------+---------+---------+---------+ 1380

| Lc743 | GTCTACTTGTATCGCTTCGACTTTGATTCGGAAGATCTTATTAATCCCTATCGTATTATG |
|---|---|
| L103A | ..............................C............................ |
| L103B | ..............................C............................ |
| L103C | ..............................C............................ |
| L103D | ..............................C............................ |

TABLE 1-continued

| | | | | | | | | | | | | | | | | | |
|---|---|---|---|---|---|---|---|---|---|---|---|---|---|---|---|---|---|
| L103con | . | . | . | . | . | . | . | . | . | . | C | . | . | . | . | . | . |
| Lc743 | R | S | G | R | G | V | K | G | V | S | H | A | D | E | L | T | Y | F | F | W |
| L103con | . | . | . | . | . | . | . | . | . | . | . | . | . | . | . | . | . | . | . | . |

```
     1381 ---------+---------+---------+---------+---------+---------+  1440
Lc743   CGTAGTGGACGTGGTGTTAAGGGTGTTAGTCATGCTGATGAATTAACCTATTTCTTCTGG
L103A   ............................................................
L103B   ............................................................
L103C   ............................................................
L103D   ............................................................
L103con ............................................................
```

| Lc743 | N | Q | L | A | K | R | M | P | K | E | S | R | E | Y | K | T | I | E | R | M |
|---|---|---|---|---|---|---|---|---|---|---|---|---|---|---|---|---|---|---|---|---|
| L103con | . | . | . | . | . | . | . | . | . | . | . | . | . | . | . | . | . | . | . | . |

```
     1441 ---------+---------+---------+---------+---------+---------+  1500
Lc743   AATCAATTGGCCAAACGTATGCCTAAAGAATCGCGTGAATACAAAACAATTGAACGTATG
L103A   ...........................C................................
L103B   ...........................C................................
L103C   ...........................C................................
L103D   ...........................C................................
L103con ...........................C................................
```

| Lc743 | T | G | I | W | I | Q | F | A | T | T | G | N | P | Y | S | N | E | I | E | G |
|---|---|---|---|---|---|---|---|---|---|---|---|---|---|---|---|---|---|---|---|---|
| L103con | . | . | . | . | . | . | . | . | . | . | . | . | . | . | . | . | . | . | . | . |

```
     1501 ---------+---------+---------+---------+---------+---------+  1560
Lc743   ACTGGTATATGGATACAATTTGCCACCACTGGTAATCCTTATAGCAATGAAATTGAAGGT
L103A   ............................................................
L103B   ............................................................
L103C   ............................................................
L103D   ............................................................
L103con ............................................................
```

| Lc743 | M | E | N | V | S | W | D | P | I | K | K | S | D | E | V | Y | K | C | L | N |
|---|---|---|---|---|---|---|---|---|---|---|---|---|---|---|---|---|---|---|---|---|
| L103con | . | . | . | . | . | . | . | . | . | . | . | . | . | . | . | . | . | . | . | . |

```
     1561 ---------+---------+---------+---------+---------+---------+  1620
Lc743   ATGGAAAATGTTTCCTGGGATCCAATTAAGAAATCCGACGAAGTATACAAGTGTTTGAAT
L103A   ........................T..............T.....G.............
L103B   ........................T..............T.....G.............
L103C   ........................T..............T.....G.............
L103D   ........................T..............T.....G.............
L103con ........................T..............T.....G.............
```

| Lc743 | I | S | D | E | L | K | M | I | D | V | P | E | M | D | K | I | K | Q | W | E |
|---|---|---|---|---|---|---|---|---|---|---|---|---|---|---|---|---|---|---|---|---|
| L103con | . | . | . | . | . | . | . | . | . | . | . | . | . | . | . | . | . | . | . | . |

```
     1621 ---------+---------+---------+---------+---------+---------+  1680
```

TABLE 1-continued

| | |
|---|---|
| Lc743 | ATTAGTGACGAATTGAAAATGATTGATGTGCCTGAAATGGATAAGATTAAACAATGGGAA |
| L103A | . . . . . C . . T . . . . . . . . . . . . . . . . . . . . . . . . . . . . . . . . . . . . . . . . . . . . . . . |
| L103B | . . . . . . . . T . . . . . . . . . . . . . . . . A . . . . . . . . . . . . . . . . . . . . . . . . . . . . . . |
| L103C | . . . . . . . . T . . . . . . . . . . . . . . . . . . . . . . . . . . . . . . . . . . . . . . . . . . . . . . . |
| L103D | . . . . . . . . T . . . . . . . . . . . . . . . . . . . . . . . . . . . . . . . . . . . . . . . . . . . . . . . |
| L103con | . . . . . . . . T . . . . . . . . . . . . . . . . . . . . . . . . . . . . . . . . . . . . . . . . . . . . . . . |

| | |
|---|---|
| Lc743 | S    M    F    E    K    H    R    D    L    F    * |
| L103con | .    .    .    .    .    .    .    .    .    . |
| 1681 | - - - - - - - - - + - - - - - - - - - + - - - - - - - - - + - - - 1713 |
| Lc743 | TCGATGTTTGAAAAACATAGAGATTTATTTTAG |
| L103A | . . . . . . . . . . . . . . . . . . . . . . . . . . . . . . . . . |
| L103B | . . . . . . . . . . . . . . . . . . . . . . . . . . . . . . . . . |
| L103C | . . . . . . . . . . . . . . . . . . . . . . . . . . . . . . . . . |
| L103D | . . . . . . . . . . . . . . . . . . . . . . . . . . . . . . . . . |
| L103con | . . . . . . . . . . . . . . . . . . . . . . . . . . . . . . . . . |

TABLE 2

Comparison of the inferred amino acid sequences of the OP sensitive E3 of *L. cuprina* (clone Lc743l top line) (SEQ ID NO:3) and its *Drosophila melanogaster* homologue, DmαE7 (bottom line).

```
  1 MNF NVS L ME KL KWKI KCI ENKFLNYRLTTNETVVAETE YGKVKGVKRLTV    50
    | |   | : : : : | : | : . . : | . | | : : .  . | | | | | | : | | | | . | : | | | | : :
  1 MNKNLGF VE RLRKRL KTI EHKVQQYRQSTNETVVADTE YGQVRGI KRLS L    50

51 YDDS YYS F EGI P YAQP P VGEL RF KAP QRP TP WDG VRDCCNHKDKS VQVDF   100
    | |     . | : | | | | | | | | | | | | | | | | |  . | : | | | | | : . . | | | . | | | . |
 51      YDVP YFS F EGI P YAQP P VGEL RF KAP QRP I PWEGVRDCS QP KDKAVQVQF   100

101 I TGKVCGS EDCL YLS VYTNNLNP ETKRP VL VYI HGGGFI I GENHRDMYGP   150
    :  : | |   | | | | | | | | .  | | | | | | | : . | : .   | | | : | :  | | | | | | | | | . : | :     | | |
101 VF DKVEGS EDCL YLNVYTNNVKP DKARP VMVWI HGGGFI I GEANREWYGP   150

151 DYF I KKDVVL I NI QYRLGAL GF LS LNS EDLNVP GNAGL KDQVMAL RWI KN   200
    | | | : | . | | | |   | : . | | | | | | | | | | | | : | |  . : | | | | | | | | | | | : | | : | | | |
151 DYF MKEDVVL VTI QYRLGAL GF MS LKS PE LNVP GNAGL KDQVL AL KWI KN   200

201 NCANF GGNP DNI TVF GES AGAAS THYMML TEQTRGL FHRGI LMS GNAI CP   250
    | | | . | | | | : | :   | | | | | | | | | | | | | | | | : | | : . | | | | | | |     | | . | | | |
201 NCAS F GGDP NCI TVF GES AGGAS THYMML TDQTQGL FHRGI LQS GS AI CP   250

251 WA. NTQCQHR AF TL AKL AGYKGE DNDKDVL EF LMKAKP QDL I KLEEKVL T   299
    | |       | . : . | . : : :   | | | . | | | | | | | | | | | | | | | . . | | | : : | | . | | |
251 WAYNGDI THNP YRI AKL VGYKGE DNDKDVL EF LQNVKAKDL I RVEENVL T   300

300 LEERTNKVMF P F GP TVEP YQTADCVL P KHP REMVKTAWGNS I P TMMGNTS   349
    | | | |   | | . | |  . | | |    . : | | |    | : : : | . | .   | | : | | | |    : : | | | |
301 LEERMNKI MF RF GP S L EP FS TPECVI S KP P KEMMKT AWS NS I PMF I GNTS   350

350 YEGLFF TS I LKQMP MLVKE LE TCVNF VP S ELADAERTAP ETLEMGAKI KK   399
    | | | | | : | | |  : | | | | : | | . | : | . | . | : . | : | | | |  . | | | | . | : : | | | . | |
351 YEGLL WVP EVKLMP QVLQQLDAGTP FI P KELL ATEP S KEKLDS WS AQI RD   400

400 AHVTGETP TADNFMDLCS HI YF WFP MHRL LQL RFNHTS GTP VYL YRF DF D   449
    . | | |  . . . | : | | | | | | | |   | | | | | |   | : : :   |  . . . . . | | | | : | | : | | |
401 VHRTGS ES TP DNYMDLCS I YYF VF P ALRVVHS RHAYAAGAP VYF YRYDF D   450

450 S EDL I NP YRI MRS GRGVKGVS HADEL TYF F WNQL AKRMP KES REYKTI ER   499
    | | : | |   | | | | | | | | | | | | | | | | | . | : . . | | : : | | | | | | | | : | | |
451 S EELI FP YRI MRMGRGVKGVS HADDLSYQF SS LL ARRLP KES REYRNI ER   500
```

TABLE 2-continued

Comparison of the inferred amino acid sequences of the OP sensitive E3 of *L. cuprina* (clone Lc743l top line) (SEQ ID NO:3) and its *Drosophila melanogaster* homologue, DmαE7 (bottom line).

```
500 MT G I  WI  Q F A T T G N P  YS NE I  E G ME N V S  WD P I  K K S  D E V Y K C L  N I  S D E L  K M I  D   549
       |  |  |    |  |  |    |  |  |  |  |  |  |    :    |  :  |  |  :  :      |  |  :  :  |  |  |  .  |    |  |  |  |  |  |    :  |  |  :  |  |
501 T V G I  WT Q F A A T G N P  YS E K I  N G M D T L T I  D P V R K S  D A V I  K C L  N I  S D D L  K F I  D   550

550 V P E MD K I  K Q WE S  MF E K H R D L F  .   570
      :  |  |    .  |  :  |     |  |  |  :  :  .  :  :  |  |  :
551 L P E WP  K L  K V WE S  L Y D D N K D L L F   572       (SEQ ID NO:8)
```

EXAMPLE 4

Sequence of an OP-Resistant Allele of LcαE7 (E3)

a) Cloning the OP-resistant allele of LcαE7 (E3).

A RT-PCR (reverse transcriptase-PCR) approach was used to clone a cDNA allele of LcαE7 from a diazinon resistant strain of *L. cuprina* (Llandillo 103) which is homozygous for the fourth chromosome.

Methods:

Adults from the Llandillo 103 strain were aged for three days before collection and stored at −70° C. RNA was prepared using a modified protocol of Chigwin et al. (Chigwin, J. M., Przybyla, A. E., MacDonald, R. J. & Rutter, W. J., 1979, Biochemistry 18, 5294). About 100 adults were thoroughly homogenised in 15 ml of solution D (4M guanidinium thiocyanate, 25 mM sodium citrate, pH 7.0, 0.5% sarkosyl, 0.1M β-mercaptoethanol) using a Sorvall Omnimix blender. The resulting homogenate was filtered through glasswool and 6 ml layered on top of 5 ml of 4.8M CsCl, made up in 10 mM EDTA, pH 8, in an SW41 ultracentrifuge tube. These were spun at 35,000 rpm in an SW41 rotor for 16hr at 15° C. The supernatent was removed and the RNA pellet resuspended in 400 μl of DEPC-treated H$_2$O. The RNA was precipitated by the addition of 800 μl of ethanol and 10 μl of 4M NaCl and stored under ethanol at −20° C. Before use the RNA pellet was washed in 75% ethanol and air dried before resuspension in DEPC-treated H$_2$O.

PolyA$^+$ RNA was prepared from 500 μg of total RNA using affinity chromatography on oligo-dT cellulose (Pharmacia; Sambrook, J., Fritsch, E. F., & Maniatis, T., 1989, Molecular Cloning: A Laboratory Manual, 2nd Edition, Cold Spring Harbor Laboratory Press, USA). The resulting mRNA (1–5 kg) was again precipitated, washed and resuspended in 20 μl of DEPC-treated H$_2$O. Oligo-dT primed cDNA was made from 1 μg of mRNA using reverse transcriptase (Superscript II, BRL) as per the manufacturers instructions in a 20 μl volumn reaction. 200 ng of cDNA was used as template in a PCR reaction using primers designed from the 5' (Lc743 5': 5' atgaatttcaacgttagtttgatgga 3') (SEQ ID NO:9) and complementry 3' (Lc743 3': 5' ctaaaataaatctc-tatgttttcaaac 3') (SEQ ID NO:10) ends of the coding region of the LcαE7 gene (clone Lc743). Reactions used the proof reading UlTma thermostable polymerase (Perkin-Elmer) and contained 500 pmoles of each primer, 40 μM of each dNTP, 10 mM Tris-HCl, pH 8.8, 10 mM KCl, 0.002% Tween 20 (v/v), 2 mM MgCl$_2$, and 200 ng of template. Two drops of mineral oil were layered over each 50 μl reaction. Six units of UlTma enzyme was added after a 5 minute "hot start" at 97° C. and was followed by 40 cycles of 35 seconds at 97° C., 1 minute at 60° C. and 2 minutes at 72 ° C. A final cycle of 72° C. for 8 minutes was included. The 1.7 kb major product was gel purified and cloned into the EcoRV cleavage site of the pBSK- plasmid vector (Stratagene) using conventional cloning techniques (Sambrook, J., Fritsch, E. F., & Maniatis, T., 1989, Molecular Cloning: A Laboratory Manual, 2nd Edition, Cold Spring Harbor Laboratory Press, USA). Ten units of the restriction enzyme EcoRV was included in ligation reactions to cleave any self-ligated vector.

b) Sequence of the OP-resistant allele of LcαE7 (E3).

Four clones were chosen for sequencing (Lc7L103 A-D), three of which were derived from independent PCR reactions. A set of twelve 21-mer sequencing primers (sequence shown below) were designed from the existing LcαE7 sequence:

| primer seq (5'-3') | primer name | 5' position in Lc743 sequence (Table 1) |
|---|---|---|
| ggatggtgtgcgtgattgttg | 7F1 (SEQ ID NO: 11) | 246 |
| aaaaggatgtggtgttgatta | 7F2 (SEQ ID NO: 12) | 465 |
| actaatgtcgggtaatgctat | 7F3 (SEQ ID NO: 13) | 723 |
| cactatgatgggtaacacttc | 7F4 (SEQ ID NO: 14) | 1026 |
| tgttacaggagaaacaccaac | 7F5 (SEQ ID NO: 15) | 1203 |
| agaatcgcgtgaatacaaaac | 7F6 (SEQ ID NO: 16) | 1468 |
| acggtataccctcaaaactgt | 7R1 (SEQ ID NO: 17) | 187 |
| tcccaaacgatattgtatgtt | 7R2 (SEQ ID NO: 18) | 505 |
| acatcatgtagtgggtagagg | 7R3 (SEQ ID NO: 19) | 686 |
| ccgaggatgtttgggtaagac | 7R4 (SEQ ID NO: 20) | 981 |
| tatcagctgttggtgtttctc | 7R5 (SEQ ID NO: 21) | 1232 |
| acgcgattctttaggcatacg | 7R6 (SEQ ID NO: 22) | 1477 |

These, in conjuction with the end primers Lc743 5' and Lc743 3', were used in dye-terminator sequencing reactions (ABI) conducted following manufacturer's instructions in 25 μl capillary tubes in a Corbett Research capillary thermal cycler, except that 50 pmoles of primer was used per reaction, a "hot start" of 96° C. for 3 minutes was included and 30 cycles were completed for each sequencing reaction. Dye primer reactions were also conducted on all four clones using the ABI M13 forward and reverse primers as per ABI protocols using the same template DNA. Sequencing reactions were resolved by electrophoresis on an ABI 370A automatic sequencing machine as per the manufacturer's instructions. This resulted in both strands being sequenced entirely.

Results:

Table 1 shows a nucleotide alignment of the four resistant clones (Lc7L103A-D) (SEQ ID NO:2) compared with the reference susceptible clone (Lc743) (SEQ ID NO:1) of LcαE7. A consensus sequence of the OP-resistant LcαE7 allele was determined (Lc7L103con). Differences between resistant clones were assumed to be errors incorporated by the UlTma polymerase.

c) Sequence of the oxyanion hole region of various LcαE7 alleles

When comparing the susceptible sequence (Lc743) with that of the resistant Llandillo 103 consensus sequence (Lc7L103con), thirteen silent and five replacement differences where identified. The positions of the five replacement differences where mapped onto the homologous positions in the primary amino acid sequence of acetylcholine esterase (AChE; Sussman, J. S., Harel, M., Frolov, F., Ocfner, C., Goldman, A., Toker, L. and Silman, I., 1991, Science 253, 872) from the electric ray, *Torpedo californica,* by aligning the primary amino acid sequence of the two proteins. The homologous amino acids where highlighted on a three-dimentional model of *T. californica* AChE. Only one replacement site difference resulted in a change in the active site region of the enzyme (oxyanion hole): the glycine to aspartic acid substitution at nucleotide position 411 (Table 1).

Methods:

This nucleotide position was then sampled over a range of strains which are homozygous for chromosome IV and of known diazinon resistance status. Genomic DNA was prepared from either eggs using the method of Davis, L. G., Dibner, M. D., and Batley, J. F., (1986. *Basic Methods in Molecular Biology,* Elsavier Science Publ. Co., New York, Section 5.3 ), or from adult flies using a C-TAB method (Crozier, Y. C., Koulianos, S. & Crozier, R. H., 1991, Experientia 47, 968–969). 1 μg samples were then used as templates in PCR reactions using .100 pmoles of the primers 7F1 (SEQ ID NO:11) and 7R4 (SEQ ID NO:20). Also included in the reactions were 0.2 mM of each dNTP, 10 mM Tris-HCl, pH 8.3, 50 mM KCl, 1.5 mM $MgCl_2$. Two drops of mineral oil were layered over each 50 μl reaction. 2.5 units of Taq polymerase was added after a "hot start" of 97° C. for 3 minutes while an annealing temperature of 55° C. was maintained. An initial extention at 72° C. was held for 2 minutes. This was followed by 34 rounds of 97° C. for 35 seconds, 55° C. for 1 minute and 72° C. for 1 minute. A final extention of 72° C. for 9 minutes was included. A single product of about 1 kb was produced. This was purified for sequencing using QIAquick spin columns (Qiagen), following manufacturer's instructions. 1 μg of template was used in dye-terminator sequencing reactions using the 7R2 (SEQ ID NO:18) primer as described above.

Results:

Of the 14 strains assayed, all seven diazinon susceptible strains (LS2, Llandillo 104, LBB101 and four malathion resistant strains, der-R, Woodside 5.2, Hampton Hill 6.1, Hampton Hill 6.2) possess a G at nucleotide postion 411, whereas all six diazinon resistant strains (Llandillo 103, Gunning 107, der-S, Q4, Sunbury 5.2, Strathfieldsaye 4.1) possess an A at this position, resulting in a Gly to Asp substitution at amino acid position 137.

EXAMPLE 4

Hydrolytic Activity of the E3 Enzyme a) In vitro expression of LcαE7 alleles

Methods:

The susceptible (clone Lc743) and resistant (clone Lc7L103D) alleles of LcαE7 were cloned into the baculovirus transfer vector, Bacpac 8 (Clonetech), 3' of the polyhedrin promoter. Transfections were conducted using a lipofection method with polybrene (Sigma) according to King, L. A. & Possee, R. D. (The Baculovirus Expression System: A Laboratory Guide, Chapman & Hall, London, 1992). One μg of DNA of each of the resulting constructs together with 200 ng of Bacpac 6 baculovirus DNA (Clonetech), linearised by digestion with the restriction enzyme BSU 36I (Progema), was incubated in a solution of hepes buffered saline containing 0.5% polybrene (Sigma) at room temperature for 10 minutes. The solution was then used to transfect a single well of a six well tissue culture plate pre-seeded 2 hr previously with $10^4$ Sf9 (*Spodoptera frugiperda*) cells in 1.5 ml Grace's medium (King, L. A. & Possee, R. D, The Baculovirus Expression System: A Laboratory Guide, Chapman & Hall, London, 1992). After 12 hr, the medium was removed, made up to 10% DMSO and placed back over the cells for 5 minutes. This was then replaced with 3 ml of Grace's medium containing 10% fetal calf serum. Construct plus polybrene, linearised virus plus polybrene and polybrene only controls were conducted in parallel with transfections. The transfections were harvested 4–5 days after infection and the cells isolated by centrifugation at 500 g for 5 minutes. Aliquots of the resulting supernatent were immediately stored on ice for the following chlorfenvinphos hydrolysis assay work or frozen at −20° C. as virion stocks.

b) Radiometric partition assay for OP hydrolysis

Methods:

Enzyme samples were diluted in 0.1M imidazole-HCl buffer pH 7.0 ("imidazole buffer") to a final volume of 25 μl. Reactions were started by the addition of 25 μl of [$^{14}$C-ethyl]-chlorfenvinphos (CFVP, 306.5 MBq/mmole, Internationale Isotope Munchen) diluted in imidazole buffer from a 7.5 mM stock solution in ethanol. The final chlorfenvinphos concentration was typically 50 or 75 μM for routine assays but can be much lower for the determination of kinetic parameters. The reaction was incubated at 30° C. and stopped by the addition of 300 μl dichloromethane and 150 gl of imidazole buffer containing 10 μM diethylphosphate (Eastman Kodak) followed by vigourous vortex mixing. The reactions were centrifuged to separate phases and 150 μl of the upper, aqueous phase was taken for scintillation counting to determine the amount of $^{14}$C-diethylphosphate produced by hydrolysis of CFVP. Incubations with boiled enzyme were also performed to control for non-enzymic hydrolysis of CFVP.

Results:

(i) Whole-fly homogenates: Assays were carried out on whole-fly homogenates using 50 μM CFVP. Homogenates derived from an OP-resistant strain of *L. cuprina* (RM2-6 [der-S]) exhibited an initial rate of hydrolysis of 7.7 pmol/min/mg protein. The boiled control hydrolysed CFVP at a rate of 0.48 pmol/min/mg protein. Homogenates derived from an OP-susceptible strain (LS2) hydrolysed CFVP at the same rate as the boiled control, indicating the absence of CFVP hydrolytic enzymic activity in OP-susceptible *L. cuprina*.

Preliminary kinetic experiments indicated a $V_{max}$ of approximately 13 pmol/min/mg protein for the hydrolysis of CFVP by homogenates derived from the resistant strain.

(ii) LcαE7 (E3) expressed in vitro: Enzyme expressed from the OP susceptible allele (Lc743) exhibited no hydrolysis of CFVP. However, this enzyme was able to hydrolyse α-naphthol acetate (αNA). In contrast, cells expressing the OP resistant allele (Lc7L103D) hydrolysed CFVP with a Vmax of approximately 2.0 nmol/min/mg protein, but did not have elevated, or indeed any, αNA hydrolytic activity.

Preliminary kinetic experiments indicated that the Km of the CFVP hydrolysing enzymes is approximately 16 μM in both the RM2-6 homogenate and cells expressing the Lc7L103D allele.

c) Radiometric partition assay for malathion hydrolysis

Methods:

Malathion carboxylesterase (MCE) activity was assayed using the partition method of Ziegler, R., Whyard, S., Downe, A. E. R., Wyatt, G. R. & Walker, V. K., (Pesticide Biochemistry and Physiology 28: 279, 1987) as modified by Whyard, S., Russell, R. J. & Walker, V. K. (Biochemical Genetics 32: 9, 1994). Supernatants (60 µl) from cell cultures containing recombinant baculovirus (as well as controls) were added to 15 µl of dilution buffer (10 mM imidazole-HCl, pH7.0) in duplicate microfuge tubes. Reactions were started by the addition of 75 µl dilution buffer containing [$^{14}$C]-malathion [Amersham; 103 mCi/mmole, 280 nCi, labelled at both the methylene carbons of the succinate moiety, adjusted to 37.5 µM by the addition of unlabelled malathion (99%; Riedel-de-Haèn Ag., Seelze, Germany]. The assay mixture was incubated at 25° C. for one hour, then 300 µl of dilution buffer was added and the undegraded malathion extracted three times with 900 µl of chloroform. The concentration of carboxylic acids of malathion in 300 µl of aqueous phase was determined by liquid scintillation. Protein concentrations in the cell supernatants were determined by the method of Bradford, M., Analytical Biochemistry 72:248 (1976) with bovine serum albumin as the standard. The non-enzymatic degradation of malathion and/or degradation by enzymes produced by the cells was corrected for by subtracting the activity of supernatant from cells infected with non-recombinant baculovirus.

Results:

Initial rates of malathion hydrolysis by the supernatant of cells expressing the OP susceptible allele, Lc473, was 3.3 pmole/min/µl from an initial concentration of 4 µM malathion. However, the enzyme is inhibited by malathion, with a half-life of about 20 minutes, in the presence of 4 µM malathion. This has been shown both by determining the amount of $^{14}$C-malathion hydrolysed after time intervals and by determining the rate of α-NA hydrolysis after of preincubation of the enzyme with non-radiolabeled malathion for various times. In the absence of malathion there was only slight loss of enzyme activity under these conditions for at least 20 hours. It is clear that greater rates of hydrolysis occur with greater concentrations of malathion but these assays did not take inhibition of the enzyme into account. Malathion hydrolysis (0.5 pmoles/min/µl) was also detected in the supernatant of cells expressing the D. melanogaster homologue, DmaE7.

The enzyme expressed from the OP resistant allele of LcαE7, Lc7L1O3D, was not tested for malathion hydrolysis because strains resistant to general OPs are susceptible to malathion (Smyth, K-A., Boyce, T. M., Russell, R. J. and Oakeshott, J. G., in preparation). The OP resistant form of LcαE7 (E3) would not therefore be expected to hydrolyse malathion.

EXAMPLE 5

Restriction Fragment Length Polymorphism (RFLP) Analysis of L. cuprina in the Vicinity of the LcαE7 (E3) Gene An effort was also made to generate accurate genomic restriction maps for a number of representatives of each of the allelic classes of LcαE7, and to examine the maps for restriction patterns which are diagnostic for resistance. This data could then form the basis of a quick screen for the OP resistance alleles among field strains of L. cuprina.

Methods:

Fourth chromosomes of L. cuprina were isolated from field and laboratory populations and made homozygous via a crossing scheme. Individual wild-caught or laboratory flies were mated to flies heterozygous for Bal IV. Bal IV is a fourth chromosome carrying the dominant, homozygous lethal mutation Sh (short setae), the recessive marker gl (golden halteres) and multiple inversions (numbers 6, 8, and 12) to suppress recombination between this chromosome and wild type chromosomes when occurring together in heterozygotes. Single Sh/+ flies from the F1 generation were crossed again to Bal IV and Sh/+ flies from that cross selfed to generate lines homozygous for the fourth chromosome.

Dose-mortality responses were determined by topical application of 1 µl of increasing concentrations of diazinon in acetone to the thorax of adult flies.

Total DNA was isolated from eggs of each strain by the method of L. G. Davis, M. D. Dibner, and J. F. Batley, (1986. *Basic Methods in Molecular Biology*, Elsavier Science Publ. Co., New York, Section 5.3 ). Restriction enzyme maps were created by single and double digestion of DNA with restriction enzymes following manufacturer's recommendations. Digested DNA was electrophoresed in 0.8% agarose gels in 0.5X TBE pH 8.0 and transferred to uncharged nylon membrane (Genescreen®) by the method of D. F. Westneat, W. A. Noon, H. K. Reeve, and C. F. Aquadro (1988. Nucleic Acids Research. 16, 4161) after acid depurination in 0.25M HCl for 7 min. The membranes were probed with $^{32}$P labeled DNA via random primed extension (A. P. Feinberg and B. Vogelstein, 1983. *Analytical Biochemistry* 132, 6–13 ) using LcαE7 cDNA as template in the hybridisation solution of Westneat et al. (1988) at 60° C. overnight. The membranes were washed in 40 mM phosphate buffer pH 7.2, 1 mM EDTA, 1% SDS twice at room temperature for 5 min., then twice at 55° C. for 15 min. prior to autoradiography.

Results:

Across all lines examined to date, three different haplotype classes have been discovered for LcαE7 using seven restriction enzymes (Table 3). Differences among haplotypes are the result of both gains and losses of restriction sites and changes in fragment sizes resulting from insertions or deletions of DNA sequence. Insertion and deletion variation occurs only within the susceptible (halplotype A) class (Table 3). Other than this size variation, there is little apparent sequence variation within each class of LcαE7 allele.

Through a combination of restriction site differences, and fragment size differences resulting from apparent insertions and deletions, haplotypes can be used to predict diazinon resistance status using the data gathered here. In particular, for most haplotypes, Eco RI restriction fragment sizes appear to be diagnostic for resistance status, and could be used to assay resistance levels in the field.

Because of the generally low amount of variation found within each haplotype class, restriction site or sequence differences discovered in cDNA sequence data from the different classes should both have value as diagnostics for diazinon resistance. However, the presence of the oxyanion hole mutation (glycine to aspartic acid at nucleotide position 411) is not completely congruent with haplotype class as defined by these restriction sites. In particular, the chromosomes of susceptible line Flinders Island B5.2a and that of the resistant line Gunning 107 appear identical at the RFLP level, although they differ in their oxyanion hole sequence. This difference, itself, however, can be used to distinguish the two alleles via restriction digests with the enzyme Hph I, which recognises the mutant sequence (GGTGAn8) but not the susceptible sequence (GGTGG . . . ) at site 411.

TABLE 3

| Line | Diazinon resistance status | Oxyanion hole residue @ 137 | Haplotype class | CFVP hydrolysis |
|---|---|---|---|---|
| Flinders Island B5.2a | Susceptible | Glycine | A | — |
| Hampton Hill 6.1 | Susceptible | Glycine | A | — |
| LS2 | Susceptible | Glycine | A' | no |
| LBB101 | Susceptible | — | A'' | — |
| Llandillo 104 | Susceptible | Glycine | A''' | — |
| der-R | Susceptible | Glycine | B | no |
| Woodside 5.2 | Susceptible | Glycine | B | — |
| RopRmal-1 | Susceptible | — | B | — |
| M27.1.4.1 | Susceptible | — | B | — |
| Belpor 1.2 | Susceptible | — | B | — |
| Gunning 107 | Resistant | Aspartic Acid | A* | — |
| Llandillo 103 | Resistant | Aspartic Acid | C | yes |
| Sunbury 5.2 | Resistant | Aspartic Acid | C | — |
| RM 2-6 (der-S) | Resistant | Aspartic Acid | C | yes |
| Strathfieldsaye 4.1 | Resistant | Aspartic Acid | C | — |
| Q4 | Resistant | Aspartic Acid | — | yes |

— indicates not yet determined.
*indicates the presence of the resistance associated mutation at nucleotide 411.
', '', ''' indicate various insertions and deletions that change fragment sizes but not homologous restriction site sequences.

As will be clear to persons skilled in the art the present inventors have developed a protocol whereby a resistant E3 esterase can be obtained in a substantially pure form. Such a purified enzyme can then be used in a probing strategy to obtain a nucleotide sequence encoding this resistant enzyme. Further, the present inventors have elucidated cDNA sequences encoding resistant E3s. The present inventors have also developed a genetic test to screen for organophosphate resistance.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

We claim:

1. An isolated and purified organophosphate (OP)-resistant E3 esterase having the amino acid sequence shown in SEQ ID NO: 4 or an ortholog thereof, wherein said OP-resistant E3 esterase has a substitution of the amino acid corresponding to the glycine residue at position 137 of the OP-sensitive E3 esterase from *Lucilia cuprina* having the amino acid sequence of SEQ ID NO: 3.

2. The OP-resistant E3 esterase as in claim 1 which is from *Lucilia cuprina.*

3. The OP-resistant E3 esterase as in claim 2 in which the E3 esterase is from one of the isochromosomal OP-resistant *L. cuprina* strains selected from the group consisting of der-S, Inverell 22, Landillo 103 and Sunbury 5.2.

4. An isolated DNA molecule comprising the nucleotide sequence shown in SEQ ID NO: 2 or an ortholog thereof, which encodes an OP-resistant E3 esterase that hydrolyses organophosphate pesticide residues, carbamate pesticide residues, or organophosphate and carbamate pesticide residues, wherein said DNA molecule encodes an OP-resistant E3 esterase having a substitution of the amino acid corresponding to the glycine residue at position 137 of the OP-sensitive E3 esterase from *L. cuprina* having the amino acid sequence of SEQ ID NO: 3.

5. The DNA molecule as in claim 4, which comprises a nucleotide sequence encoding an OP-resistant E3 esterase from an OP-resistant strain of *L. cuprina.*

6. A transformed cell that expresses OP-resistant E3 esterase, which cell is transformed with a DNA molecule as in claim 4.

7. The transformed cell as in claim 6, which is a prokaryotic cell or an insect cell.

8. An isolated OP-resistant E3 esterase produced by a transformed cell as in claim 6.

9. A method of completely degrading or rendering less active organophosphate pesticide residues, carbamate pesticide residues, or organophosphate and carbamate pesticide residues in a contaminated sample or substance, which comprises contacting the sample or substance with an OP-resistant E3 esterase as in claim 1.

10. A method of completely degrading or rendering less active organophosphate pesticide residues, carbamate pesticide residues, or organophosphate and carbamate pesticide residues in a contaminated sample or substance, which comprises contacting the sample or substance with an OP-resistant E3 esterase encoded by the DNA molecule as in claim 4.

11. A method of completely degrading or rendering less active organophosphate pesticide residues, carbamate pesticide residues, or organophosphate and carbamate pesticide residues in a contaminated sample or substance, which comprises contacting the sample or substance with an OP-resistant E3 esterase encoded by the DNA molecule as in claim 5.

12. A method of completely degrading or rendering less active organophosphate pesticide residues, carbamate pesticide residues, or organophosphate and carbamate pesticide residues in a contaminated sample or substance, which comprises contacting the sample or substance with an OP-resistant E3 esterase encoded by the transformed cell as in claim 6.

13. A method of determining the susceptibility of a strain of *L. cuprina* to organophosphates comprising:

isolating and cloning from the strain the gene encoding E3 esterase; and comparing the sequence of the E3 encoding gene with gene LcαE7 encoding OP-sensitive E3 esterase.

14. The method as in claim 13 in which the determination is by restriction fragment length polymorphisms (RFLP) comprising:

extracting total DNA from the strain;

subjecting the extracted DNA to digestion with at least one restriction enzyme;

separating the digestion fragments to form a pattern; and comparing the pattern with the pattern of LcαE7 subjected to the same digestion.

15. An isolated and purified OP-resistant E3 esterase which has a substitution of the amino acid corresponding to the glycine residue at position 137 of the OP-sensitive E3 esterase from *L. cuprina* having the amino acid sequence of SEQ ID NO: 3.

16. The OP-resistant E3 esterase as in claim 15, wherein the amino acid substitution is glycine to aspartic acid.

17. The OP-resistant E3 esterase of claim 1, which is from a species of Diptera.

* * * * *

SEQUENCE LISTING ( 1 ) GENERAL INFORMATION:

( i i i ) NUMBER OF SEQUENCES: 22

( 2 ) INFORMATION FOR SEQ ID NO:1:

( i ) SEQUENCE CHARACTERISTICS:
( A ) LENGTH: 1713 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:1:

```
ATGAATTTCA  ACGTTAGTTT  GATGGAGAAA  TTAAAATGGA  AGATTAAATG  CATTGAAAAT        60

AAGTTTTTAA  ACTATCGTTT  AACTACCAAT  GAAACGGTGG  TAGCTGAAAC  TGAATATGGC       120

AAAGTGAAAG  GCGTTAAACG  TTTAACTGTG  TACGATGATT  CCTACTACAG  TTTTGAGGGT       180

ATACCGTACG  CCCAACCGCC  AGTGGGTGAG  CTGAGATTTA  AAGCACCCCA  GCGACCAACA       240

CCCTGGGATG  GTGTGCGTGA  TTGTTGCAAT  CATAAAGATA  AGTCAGTGCA  AGTTGATTTT       300

ATAACGGGCA  AAGTGTGTGG  CTCAGAGGAT  TGTCTATACC  TAAGTGTCTA  TACGAATAAT       360

CTAAATCCCG  AAACTAAACG  TCCCGTTTTA  GTATACATAC  ATGGTGGTGG  TTTTATTATC       420

GGTGAAAATC  ATCGTGATAT  GTATGGTCCT  GATTATTTCA  TTAAAAAGGA  TGTGGTGTTG       480

ATTAACATAC  AATATCGTTT  GGGAGCTCTA  GGTTTTCTAA  GTTAAATTC   AGAAGACCTT       540

AATGTGCCCG  GTAATGCCGG  CCTTAAAGAT  CAAGTCATGG  CCTTGCGTTG  GATTAAAAAT       600

AATTGCGCCA  ACTTTGGTGG  CAATCCCGAT  AATATTACAG  TCTTTGGTGA  AAGTGCCGGT       660
```

-continued

| | | | | | | |
|---|---|---|---|---|---|---|
| GCTGCCTCTA | CCCACTACAT | GATGTTAACC | GAACAAACTC | GCGGTCTTTT | CCATCGTGGT | 720 |
| ATACTAATGT | CGGGTAATGC | TATTTGTCCA | TGGGCTAATA | CCCAATGTCA | ACATCGTGCC | 780 |
| TTCACCTTAG | CCAAATTGGC | CGGCTATAAG | GGTGAGGATA | ATGATAAGGA | TGTTTTGGAA | 840 |
| TTTCTTATGA | AAGCCAAGCC | ACAGGATTTA | ATAAACTTG | AGGAAAAGT | TTTAACTCTA | 900 |
| GAAGAGCGTA | CAAATAAGGT | CATGTTTCCT | TTTGGTCCCA | CTGTTGAGCC | ATATCAGACC | 960 |
| GCTGATTGTG | TCTTACCCAA | ACATCCTCGG | GAAATGGTTA | AAACTGCTTG | GGGTAATTCG | 1020 |
| ATACCCACTA | TGATGGGTAA | CACTTCATAT | GAGGGTCTAT | TTTTCACTTC | AATTCTTAAG | 1080 |
| CAAATGCCTA | TGCTTGTTAA | GGAATTGGAA | ACTTGTGTCA | ATTTGTGCC | AAGTGAATTG | 1140 |
| GCTGATGCTG | AACGCACCGC | CCCAGAGACC | TTGGAAATGG | GTGCTAAAAT | TAAAAGGCT | 1200 |
| CATGTTACAG | GAGAAACACC | AACAGCTGAT | AATTTATGG | ATCTTGCTC | TCACATCTAT | 1260 |
| TTCTGGTTCC | CCATGCATCG | TTTGTTGCAA | TTACGTTTCA | ATCACACCTC | CGGTACACCC | 1320 |
| GTCTACTTGT | ATCGCTTCGA | CTTTGATTCG | GAAGATCTTA | TTAATCCCTA | TCGTATTATG | 1380 |
| CGTAGTGGAC | GTGGTGTTAA | GGGTGTTAGT | CATGCTGATG | AATTAACCTA | TTTCTTCTGG | 1440 |
| AATCAATTGG | CCAAACGTAT | GCCTAAAGAA | TCGCGTGAAT | ACAAACAAT | TGAACGTATG | 1500 |
| ACTGGTATAT | GGATACAATT | TGCCACCACT | GGTAATCCTT | ATAGCAATGA | AATTGAAGGT | 1560 |
| ATGGAAAATG | TTTCCTGGGA | TCCAATTAAG | AAATCCGACG | AAGTATACAA | GTGTTTGAAT | 1620 |
| ATTAGTGACG | AATTGAAAAT | GATTGATGTG | CCTGAAATGG | ATAAGATTAA | ACAATGGGAA | 1680 |
| TCGATGTTTG | AAAAACATAG | AGATTTATTT | TAG | | | 1713 |

( 2 ) INFORMATION FOR SEQ ID NO:2:

( i ) SEQUENCE CHARACTERISTICS:
        ( A ) LENGTH: 1713 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

| | | | | | | |
|---|---|---|---|---|---|---|
| ATGAATTTCA | ACGTTAGTTT | GATGGAGAAA | TTAAAATGGA | AGATTAAATG | CATTGAAAAT | 60 |
| AAGTTTTTAA | ACTANCGTTT | AACTACCAAT | GAAACGGTGG | TAGCTGAAAC | TGAATATGGC | 120 |
| AAAGTGAAAG | GCGTTAAACG | TTTAACTGTG | TACGATGATT | CCTACTACAG | TTTTGAGGGT | 180 |
| ATACCGTACG | CCCAACCGCC | AGTGGGTGAG | CTGAGATTTA | AAGCACCCCA | GCGACNAACA | 240 |
| CCCTGGGATG | GTGTGCGTGA | TTGTTGCAAT | CATAAAGATA | AGTCAGTGCA | AGTTGATTTT | 300 |
| ATNACNGGCA | AAGTGTGTGG | CTCAGAGGAT | TGTCTATACC | TAAGNGTCTA | TACGAATAAT | 360 |
| CTAAATCCCG | AAACTAAACG | TCCCGTTTTA | GTATACATAC | ATGGTGGTGN | TTTTATTATC | 420 |
| GGTGAAAATC | ATCGTGNTAT | GTATGGTCCT | GATTATTTCA | TTAAAAGGA | TGTGGTGTTG | 480 |
| ATTAACATAC | AATATCGTTT | GGGAGCTCTA | GGTTTTCTAA | GTTTAAATTC | AGAAGACCTT | 540 |
| AATGTGCCCN | GTAATGCCGG | CCTTAAAGAT | CAAGTCATGG | CCTTGCGTTG | GATTAAAAAT | 600 |
| AATTGCGCCA | ACTTTGGTGG | CAATCCCGAT | AATATTACAG | TCTTTGGTGA | AAGTGCCGGT | 660 |
| GCTGCCTCTA | CCCACTACAT | GATGTTAACC | GAACAAACTC | GCGGTCTTTT | CCATCGTGGT | 720 |
| ATACTAATGT | CGGGTAATGC | TATTNGTCCA | TGGGCTAATA | CCCAATGTCA | ACATCGTGCC | 780 |
| TTCACCTTAG | CCAAATTGGN | CGGCTATAAG | GGTGAGGATA | ATGATAAGGA | TGTTTTGGAN | 840 |
| TTTCTTNTGA | AAGCCAAGCC | ACAGGATTTA | ATAAACTTG | AGGAAAAGT | TTTAACTCTA | 900 |
| GAAGAGCGTA | CAAATAAGGT | CATGTTTCCT | TTTGGTCCCA | CTGTTGANCC | ATATCAGACC | 960 |

```
GCTGATTGTG  TCTTACCCAA  ACATCCTCGG  GAAATGGTTA  AANNTGCTTG  GGGTAATTCG      1020

ATACCCACTA  TGATGGGTAA  CACTTCATAT  GAGGGTCTAT  TTTTCACTTC  NNTTCTTAAG      1080

CAAATGCCTA  TGCTTGTTAA  GGAATTGGAA  ACTTGTGTCA  ATTTTGTGCC  AAGTGAATTG      1140

GCTGATNCTG  AACGCACCGC  CCCAGAGACC  TTGGAAATGG  GTGCTAAAAT  TAAAAGGCT       1200

CATGTTACAG  GAGAAACACC  AACNGCNGAT  AATTTTATGG  ATCTTTGCTC  TCACATCTAT      1260

TTCTGGTTCC  CCATGCATCG  TTTNTTGCAA  TTACGTTTCA  ATCACNCCTC  CGGTACACCC      1320

GTCTACTTGT  ATCGCTTCGA  CTTNGATTCG  GAAGATCTTA  TTAATCCCTA  TCGTATTATG      1380

CGTAGTGGAC  GTGGTGTTAA  GGGTGTTAGT  CATGCTGATG  AATTAACCTA  TTTCTTCTGG      1440

AATCAATTGG  CCAAACGTAT  GCCTAAAGAA  TCNCGTGAAT  ACAAAACAAT  TGAACGTATG      1500

ACTGGTATAT  GGATACAATT  TGCCACCACT  GGTAATCCTT  ATAGCAATGA  AATTGAAGGT      1560

ATGGAAAATG  TTTCCTGGGA  TCNAATTAAG  AAATCCGANG  AAGTNTACAA  GTGTTTGAAT      1620

ATTAGNGANG  AATTGAAAAT  GATTGATGNG  CCTGAAATGG  ATAAGATTAA  ACAATGGGAA      1680

TCGATGTTTG  AAAAACATAG  AGATTTATTT  TAG                                    1713
```

(2) INFORMATION FOR SEQ ID NO:3:

(i) SEQUENCE CHARACTERISTICS:
        (A) LENGTH: 570 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

```
Met  Asn  Phe  Asn  Val  Ser  Leu  Met  Glu  Lys  Leu  Arg  Trp  Lys  Ile  Arg
  1              5                  10                      15

Cys  Ile  Glu  Asn  Lys  Phe  Leu  Asn  Tyr  Arg  Leu  Thr  Thr  Asn  Glu  Thr
              20                  25                      30

Val  Val  Ala  Glu  Thr  Glu  Tyr  Gly  Lys  Val  Lys  Gly  Val  Lys  Arg  Leu
          35                  40                      45

Thr  Val  Tyr  Asp  Asp  Ser  Tyr  Tyr  Ser  Phe  Glu  Gly  Ile  Pro  Tyr  Ala
      50                  55                      60

Gln  Pro  Pro  Val  Gly  Glu  Leu  Arg  Phe  Lys  Ala  Pro  Gln  Arg  Pro  Thr
 65                  70                  75                          80

Pro  Trp  Asp  Gly  Val  Arg  Asp  Cys  Cys  Asn  His  Lys  Asp  Lys  Ser  Val
              85                  90                      95

Gln  Val  Asp  Phe  Ile  Thr  Gly  Lys  Val  Cys  Gly  Ser  Glu  Asp  Cys  Leu
              100                 105                     110

Tyr  Leu  Ser  Val  Tyr  Thr  Asn  Asn  Leu  Asn  Pro  Glu  Thr  Lys  Arg  Pro
              115                 120                     125

Val  Leu  Val  Tyr  Ile  His  Gly  Gly  Phe  Ile  Ile  Gly  Glu  Asn  His
          130                 135                     140

Arg  Asp  Met  Tyr  Gly  Pro  Asp  Tyr  Phe  Ile  Lys  Lys  Asp  Val  Val  Leu
 145                 150                 155                         160

Ile  Asn  Ile  Gln  Tyr  Arg  Leu  Gly  Ala  Leu  Gly  Phe  Leu  Ser  Leu  Asn
                  165                 170                     175

Ser  Glu  Asp  Leu  Asn  Val  Pro  Gly  Asn  Ala  Gly  Leu  Lys  Asp  Gln  Val
              180                 185                     190

Met  Ala  Leu  Arg  Trp  Ile  Lys  Asn  Asn  Cys  Ala  Asn  Phe  Gly  Gly  Asn
          195                 200                     205

Pro  Asp  Asn  Ile  Thr  Val  Phe  Gly  Glu  Ser  Ala  Gly  Ala  Ala  Ser  Thr
```

-continued

|  |  |  |  |  | 210 |  |  |  |  | 215 |  |  |  |  | 220 |  |  |
|---|---|---|---|---|---|---|---|---|---|---|---|---|---|---|---|---|---|
| His 225 | Tyr | Met | Met | Leu | Thr 230 | Glu | Gln | Thr | Arg | Gly 235 | Leu | Phe | His | Arg | Gly 240 |
| Ile | Leu | Met | Ser | Gly 245 | Asn | Ala | Ile | Cys | Pro 250 | Trp | Ala | Asn | Thr | Gln 255 | Cys |
| Gln | His | Arg | Ala 260 | Phe | Thr | Leu | Ala | Lys 265 | Leu | Ala | Gly | Tyr | Lys 270 | Gly | Glu |
| Asp | Asn | Asp 275 | Lys | Asp | Val | Leu | Glu 280 | Phe | Leu | Met | Lys | Ala 285 | Lys | Pro | Gln |
| Asp | Leu | Ile 290 | Lys | Leu | Glu | Glu 295 | Lys | Val | Leu | Thr | Leu 300 | Glu | Glu | Arg | Thr |
| Asn 305 | Lys | Val | Met | Phe | Pro 310 | Phe | Gly | Pro | Thr | Val 315 | Glu | Pro | Tyr | Gln | Thr 320 |
| Ala | Asp | Cys | Val | Leu 325 | Pro | Lys | His | Pro | Arg 330 | Glu | Met | Val | Lys | Thr 335 | Ala |
| Trp | Gly | Asn | Ser 340 | Ile | Pro | Thr | Met | Met 345 | Gly | Asn | Thr | Ser | Tyr 350 | Glu | Gly |
| Leu | Phe | Phe 355 | Thr | Ser | Ile | Leu | Lys 360 | Gln | Met | Pro | Met | Leu 365 | Val | Lys | Glu |
| Leu | Glu 370 | Thr | Cys | Val | Asn | Phe 375 | Val | Pro | Ser | Glu | Leu 380 | Ala | Asp | Ala | Glu |
| Arg 385 | Thr | Ala | Pro | Glu | Thr 390 | Leu | Glu | Met | Gly | Ala 395 | Lys | Ile | Lys | Lys | Ala 400 |
| His | Val | Thr | Gly | Glu 405 | Thr | Pro | Thr | Ala | Asp 410 | Asn | Phe | Met | Asp | Leu 415 | Cys |
| Ser | His | Ile | Tyr 420 | Phe | Trp | Phe | Pro | Met 425 | His | Arg | Leu | Leu | Gln 430 | Leu | Arg |
| Phe | Asn | His 435 | Thr | Ser | Gly | Thr | Pro 440 | Val | Tyr | Leu | Tyr | Arg 445 | Phe | Asp | Phe |
| Asp | Ser 450 | Glu | Asp | Leu | Ile | Asn 455 | Pro | Tyr | Arg | Ile | Met 460 | Arg | Ser | Gly | Arg |
| Gly 465 | Val | Lys | Gly | Val | Ser 470 | His | Ala | Asp | Glu | Leu 475 | Thr | Tyr | Phe | Phe | Trp 480 |
| Asn | Gln | Leu | Ala | Lys 485 | Arg | Met | Pro | Lys | Glu 490 | Ser | Arg | Glu | Tyr | Lys 495 | Thr |
| Ile | Glu | Arg | Met 500 | Thr | Gly | Ile | Trp | Ile 505 | Gln | Phe | Ala | Thr | Thr 510 | Gly | Asn |
| Pro | Tyr | Ser 515 | Asn | Glu | Ile | Glu | Gly 520 | Met | Glu | Asn | Val | Ser 525 | Trp | Asp | Pro |
| Ile | Lys 530 | Lys | Ser | Asp | Glu | Val 535 | Tyr | Lys | Cys | Leu | Asn 540 | Ile | Ser | Asp | Glu |
| Leu | Lys 545 | Met | Ile | Asp | Val | Pro 550 | Glu | Met | Asp | Lys | Ile 555 | Lys | Gln | Trp | Glu 560 |
| Ser | Met | Phe | Glu | Lys 565 | His | Arg | Asp | Leu | Phe 570 |

( 2 ) INFORMATION FOR SEQ ID NO:4:

( i ) SEQUENCE CHARACTERISTICS:
        ( A ) LENGTH: 570 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:4:

| | | | | | | | | | | | | | | |
|---|---|---|---|---|---|---|---|---|---|---|---|---|---|---|
| Met<br>1 | Asn | Phe | Asn | Val<br>5 | Ser | Leu | Met | Glu | Lys<br>10 | Leu | Arg | Trp | Lys | Ile<br>15 | Arg |
| Cys | Ile | Glu | Asn<br>20 | Lys | Phe | Leu | Asn | Tyr<br>25 | Arg | Leu | Thr | Thr | Asn<br>30 | Glu | Thr |
| Val | Val | Ala<br>35 | Glu | Thr | Glu | Tyr | Gly<br>40 | Lys | Val | Lys | Gly | Val<br>45 | Lys | Arg | Leu |
| Thr | Val<br>50 | Tyr | Asp | Asp | Ser | Tyr<br>55 | Tyr | Ser | Phe | Glu | Gly<br>60 | Ile | Pro | Tyr | Ala |
| Gln<br>65 | Pro | Pro | Val | Gly | Glu<br>70 | Leu | Arg | Phe | Lys | Ala<br>75 | Pro | Gln | Arg | Pro | Thr<br>80 |
| Pro | Trp | Asp | Gly | Val<br>85 | Arg | Asp | Cys | Cys | Asn<br>90 | His | Lys | Asp | Lys | Ser<br>95 | Val |
| Gln | Val | Asp | Phe<br>100 | Ile | Thr | Gly | Lys | Val<br>105 | Cys | Gly | Ser | Glu | Asp<br>110 | Cys | Leu |
| Tyr | Leu | Ser<br>115 | Val | Tyr | Thr | Asn | Asn<br>120 | Leu | Asn | Pro | Glu | Thr<br>125 | Lys | Arg | Pro |
| Val | Leu<br>130 | Val | Tyr | Ile | His | Gly<br>135 | Gly | Xaa | Phe | Ile | Ile<br>140 | Gly | Glu | Asn | His |
| Arg<br>145 | Asp | Met | Tyr | Gly | Pro<br>150 | Asp | Tyr | Phe | Ile | Lys<br>155 | Lys | Asp | Val | Val | Leu<br>160 |
| Ile | Asn | Ile | Gln | Tyr<br>165 | Arg | Leu | Gly | Ala | Leu<br>170 | Gly | Phe | Leu | Ser | Leu<br>175 | Asn |
| Ser | Glu | Asp | Leu<br>180 | Asn | Val | Pro | Gly | Asn<br>185 | Ala | Gly | Leu | Lys | Asp<br>190 | Gln | Val |
| Met | Ala | Leu | Arg<br>195 | Trp | Ile | Lys | Asn | Asn<br>200 | Cys | Ala | Asn | Phe | Gly<br>205 | Gly | Asn |
| Pro | Asp<br>210 | Asn | Ile | Thr | Val | Phe<br>215 | Gly | Glu | Ser | Ala | Gly<br>220 | Ala | Ala | Ser | Thr |
| His<br>225 | Tyr | Met | Met | Leu | Thr<br>230 | Glu | Gln | Thr | Arg | Gly<br>235 | Leu | Phe | His | Arg | Gly<br>240 |
| Ile | Leu | Met | Ser | Gly<br>245 | Asn | Ala | Ile | Cys | Pro<br>250 | Trp | Ala | Asn | Thr | Gln<br>255 | Cys |
| Gln | His | Arg | Ala<br>260 | Phe | Thr | Leu | Ala | Lys<br>265 | Leu | Xaa | Gly | Tyr | Lys<br>270 | Gly | Glu |
| Asp | Asn | Asp<br>275 | Lys | Asp | Val | Leu | Glu<br>280 | Phe | Leu | Xaa | Lys | Ala<br>285 | Lys | Pro | Gln |
| Asp | Leu | Ile<br>290 | Lys | Leu | Glu | Glu | Lys<br>295 | Val | Leu | Thr | Leu | Glu<br>300 | Glu | Arg | Thr |
| Asn | Lys<br>305 | Val | Met | Phe | Pro | Phe<br>310 | Gly | Pro | Thr | Val | Glu<br>315 | Pro | Tyr | Gln | Thr<br>320 |
| Ala | Asp | Cys | Val | Leu<br>325 | Pro | Lys | His | Pro | Arg<br>330 | Glu | Met | Val | Lys | Xaa<br>335 | Ala |
| Trp | Gly | Asn | Ser | Ile<br>340 | Pro | Thr | Met | Met | Gly<br>345 | Asn | Thr | Ser | Tyr | Glu<br>350 | Gly |
| Leu | Phe | Phe<br>355 | Thr | Ser | Xaa | Leu | Lys<br>360 | Gln | Met | Pro | Met | Leu<br>365 | Val | Lys | Glu |
| Leu | Glu<br>370 | Thr | Cys | Val | Asn | Phe<br>375 | Val | Pro | Ser | Glu | Leu<br>380 | Ala | Asp | Ala | Glu |
| Arg<br>385 | Thr | Ala | Pro | Glu | Thr<br>390 | Leu | Glu | Met | Gly | Ala<br>395 | Lys | Ile | Lys | Lys | Ala<br>400 |
| His | Val | Thr | Gly | Glu<br>405 | Thr | Pro | Thr | Ala | Asp<br>410 | Asn | Phe | Met | Asp | Leu<br>415 | Cys |
| Ser | His | Ile | Tyr | Phe | Trp | Phe | Pro | Met | His | Arg | Leu | Leu | Gln | Leu | Arg |

-continued

```
                           420                          425                          430
         Phe  Asn  His  Thr  Ser  Gly  Thr  Pro  Val  Tyr  Leu  Tyr  Arg  Phe  Asp  Phe
                   435                     440                     445

Asp  Ser  Glu  Asp  Leu  Ile  Asn  Pro  Tyr  Arg  Ile  Met  Arg  Ser  Gly  Arg
              450                     455                     460

Gly  Val  Lys  Gly  Val  Ser  His  Ala  Asp  Glu  Leu  Thr  Tyr  Phe  Phe  Trp
         465                     470                     475                          480

Asn  Gln  Leu  Ala  Lys  Arg  Met  Pro  Lys  Glu  Ser  Arg  Glu  Tyr  Lys  Thr
                             485                     490                          495

Ile  Glu  Arg  Met  Thr  Gly  Ile  Trp  Ile  Gln  Phe  Ala  Thr  Thr  Gly  Asn
                        500                     505                     510

Pro  Tyr  Ser  Asn  Glu  Ile  Glu  Gly  Met  Glu  Asn  Val  Ser  Trp  Asp  Pro
                   515                     520                     525

Ile  Lys  Lys  Ser  Asp  Glu  Val  Tyr  Lys  Cys  Leu  Asn  Ile  Ser  Asp  Glu
              530                     535                     540

Leu  Lys  Met  Ile  Asp  Val  Pro  Glu  Met  Asp  Lys  Ile  Lys  Gln  Trp  Glu
         545                     550                     555                          560

Ser  Met  Phe  Glu  Lys  His  Arg  Asp  Leu  Phe
                             565                     570
```

(2) INFORMATION FOR SEQ ID NO:5:

(i) SEQUENCE CHARACTERISTICS:
        (A) LENGTH: 32 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

```
         Gly  Gly  Ile  Trp  Ser  Ile  Gly  Ala  Arg  Gly  Ala  Tyr  Thr  Gly  Tyr  Tyr
         1                   5                        10                          15

Thr  Ile  Thr  Ala  Tyr  Tyr  Thr  Asn  Ala  Ala  Tyr  Gly  Thr  Asn  Thr  Ala
                             20                      25                          30
```

(2) INFORMATION FOR SEQ ID NO:6:

(i) SEQUENCE CHARACTERISTICS:
        (A) LENGTH: 30 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

```
         Tyr  Thr  Gly  Arg  Thr  Cys  Tyr  Thr  Thr  Ile  Ala  Arg  Ile  Cys  Cys  Ile
         1                   5                        10                          15

Gly  Cys  Arg  Thr  Thr  Asn  Cys  Cys  Asn  Gly  Gly  Asn  Ala  Cys
                             20                      25                      30
```

(2) INFORMATION FOR SEQ ID NO:7:

(i) SEQUENCE CHARACTERISTICS:
        (A) LENGTH: 26 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:7:

Ala Thr His Cys Cys Ile Thr Trp Thr Gly Cys Ile Val Met Ile Cys
1               5                   10                  15

Cys Ile Cys Cys Ile Asx Thr Asn Gly Gly
            20              25

( 2 ) INFORMATION FOR SEQ ID NO:8:

( i ) SEQUENCE CHARACTERISTICS:
( A ) LENGTH: 572 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:8:

Met Asn Lys Asn Leu Gly Phe Val Glu Arg Leu Arg Lys Arg Leu Lys
1               5                   10                  15

Thr Ile Glu His Lys Val Gln Gln Tyr Arg Gln Ser Thr Asn Glu Thr
                20                  25                  30

Val Val Ala Asp Thr Glu Tyr Gly Gln Val Arg Gly Ile Lys Arg Leu
            35                  40                  45

Ser Leu Tyr Asp Val Pro Tyr Phe Ser Phe Glu Gly Ile Pro Tyr Ala
50                      55                  60

Gln Pro Pro Val Gly Glu Leu Arg Phe Lys Ala Pro Gln Arg Pro Ile
65                  70                  75                  80

Pro Trp Glu Gly Val Arg Asp Cys Ser Gln Pro Lys Asp Lys Ala Val
                85                  90                  95

Gln Val Gln Phe Val Phe Asp Lys Val Glu Gly Ser Glu Asp Cys Leu
            100                 105                 110

Tyr Leu Asn Val Tyr Thr Asn Asn Val Lys Pro Asp Lys Ala Arg Pro
            115                 120                 125

Val Met Val Trp Ile His Gly Gly Phe Ile Ile Gly Glu Ala Asn
    130                 135                 140

Arg Glu Trp Tyr Gly Pro Asp Tyr Phe Met Lys Glu Asp Val Val Leu
145                 150                 155                 160

Val Thr Ile Gln Tyr Arg Leu Gly Ala Leu Gly Phe Met Ser Leu Lys
                165                 170                 175

Ser Pro Glu Leu Asn Val Pro Gly Asn Ala Gly Leu Lys Asp Gln Val
            180                 185                 190

Leu Ala Leu Lys Trp Ile Lys Asn Asn Cys Ala Ser Phe Gly Gly Asp
            195                 200                 205

Pro Asn Cys Ile Thr Val Phe Gly Glu Ser Ala Gly Gly Ala Ser Thr
    210                 215                 220

His Tyr Met Met Leu Thr Asp Gln Thr Gln Gly Leu Phe His Arg Gly
225                 230                 235                 240

Ile Leu Gln Ser Gly Ser Ala Ile Cys Pro Trp Ala Tyr Asn Gly Asp
                245                 250                 255

Ile Thr His Asn Pro Tyr Arg Ile Ala Lys Leu Val Gly Tyr Lys Gly
            260                 265                 270

Glu Asp Asn Asp Lys Asp Val Leu Glu Phe Leu Gln Asn Val Lys Ala
            275                 280                 285

Lys Asp Leu Ile Arg Val Glu Glu Asn Val Leu Thr Leu Glu Glu Arg
            290                 295                 300

Met Asn Lys Ile Met Phe Arg Phe Gly Pro Ser Leu Glu Pro Phe Ser
305                 310                 315                 320

Thr Pro Glu Cys Val Ile Ser Lys Pro Pro Lys Glu Met Met Lys Thr

|     |     |     |     | 325 |     |     |     | 330 |     |     |     | 335 |     |     |
|-----|-----|-----|-----|-----|-----|-----|-----|-----|-----|-----|-----|-----|-----|-----|
| Ala | Trp | Ser | Asn<br>340 | Ser | Ile | Pro | Met | Phe<br>345 | Ile | Gly | Asn | Thr | Ser<br>350 | Tyr | Glu |
| Gly | Leu | Leu<br>355 | Trp | Val | Pro | Glu<br>360 | Val | Lys | Leu | Met | Pro<br>365 | Gln | Val | Leu | Gln |
| Gln | Leu | Asp | Ala | Gly | Thr<br>375 | Pro | Phe | Ile | Pro | Lys<br>380 | Glu | Leu | Leu | Ala | Thr |
| | 370 | | | | | | | | | | | | | | |
| Glu<br>385 | Pro | Ser | Lys | Glu | Lys<br>390 | Leu | Asp | Ser | Trp | Ser<br>395 | Ala | Gln | Ile | Arg | Asp<br>400 |
| Val | His | Arg | Thr | Gly<br>405 | Ser | Glu | Ser | Thr | Pro<br>410 | Asp | Asn | Tyr | Met | Asp<br>415 | Leu |
| Cys | Ser | Ile | Tyr<br>420 | Tyr | Phe | Val | Phe | Pro<br>425 | Ala | Leu | Arg | Val | Val<br>430 | His | Ser |
| Arg | His | Ala<br>435 | Tyr | Ala | Ala | Gly | Ala<br>440 | Pro | Val | Tyr | Phe | Tyr<br>445 | Arg | Tyr | Asp |
| Phe | Asp<br>450 | Ser | Glu | Glu | Leu | Ile<br>455 | Phe | Pro | Tyr | Arg | Ile<br>460 | Met | Arg | Met | Gly |
| Arg<br>465 | Gly | Val | Lys | Gly | Val<br>470 | Ser | His | Ala | Asp | Asp<br>475 | Leu | Ser | Tyr | Gln | Phe<br>480 |
| Ser | Ser | Leu | Leu | Ala<br>485 | Arg | Arg | Leu | Pro | Lys<br>490 | Glu | Ser | Arg | Glu | Tyr<br>495 | Arg |
| Asn | Ile | Glu | Arg<br>500 | Thr | Val | Gly | Ile | Trp<br>505 | Thr | Gln | Phe | Ala | Ala<br>510 | Thr | Gly |
| Asn | Pro | Tyr<br>515 | Ser | Glu | Lys | Ile | Asn<br>520 | Gly | Met | Asp | Thr | Leu<br>525 | Thr | Ile | Asp |
| Pro | Val<br>530 | Arg | Lys | Ser | Asp | Ala<br>535 | Val | Ile | Lys | Cys | Leu<br>540 | Asn | Ile | Ser | Asp |
| Asp<br>545 | Leu | Lys | Phe | Ile | Asp<br>550 | Leu | Pro | Glu | Trp | Pro<br>555 | Lys | Leu | Lys | Val | Trp<br>560 |
| Glu | Ser | Leu | Tyr | Asp<br>565 | Asp | Asn | Lys | Asp | Leu<br>570 | Leu | Phe | | | | |

( 2 ) INFORMATION FOR SEQ ID NO:9:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

ATGAATTTCA ACGTTAGTTT GATGGA                                             26

( 2 ) INFORMATION FOR SEQ ID NO:10:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

CTAAAATAAA TCTCTATGTT TTTCAAAC                                         28

( 2 ) INFORMATION FOR SEQ ID NO:11:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:11:

GGATGGTGTG CGTGATTGTT G        21

( 2 ) INFORMATION FOR SEQ ID NO:12:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

AAAAGGATGT GGTGTTGATT A        21

( 2 ) INFORMATION FOR SEQ ID NO:13:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:13:

ACTAATGTCG GGTAATGCTA T        21

( 2 ) INFORMATION FOR SEQ ID NO:14:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:14:

CACTATGATG GGTAACACTT C        21

( 2 ) INFORMATION FOR SEQ ID NO:15:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:15:

TGTTACAGGA GAAACACCAA C        21

( 2 ) INFORMATION FOR SEQ ID NO:16:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:16:

AGAATCGCGT GAATACAAAA C                          21

( 2 ) INFORMATION FOR SEQ ID NO:17:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:17:

ACGGTATACC CTCAAAACTG T                          21

( 2 ) INFORMATION FOR SEQ ID NO:18:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:18:

TCCCAAACGA TATTGTATGT T                          21

( 2 ) INFORMATION FOR SEQ ID NO:19:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:19:

ACATCATGTA GTGGGTAGAG G                          21

( 2 ) INFORMATION FOR SEQ ID NO:20:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:20:

CCGAGGATGT TTGGGTAAGA C                          21

( 2 ) INFORMATION FOR SEQ ID NO:21:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:21:

-continued

TATCAGCTGT TGGTGTTTCT C 21

( 2 ) INFORMATION FOR SEQ ID NO:22:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:22:

ACGCGATTCT TTAGGCATAC G 21